(12) United States Patent
Alexander

(10) Patent No.: US 10,417,758 B1
(45) Date of Patent: Sep. 17, 2019

(54) SYSTEM AND METHOD FOR REMOTELY SUPERVISING AND VERIFYING PHARMACY FUNCTIONS

(71) Applicant: Becton, Dickinson and Company, Franklin Lakes, NJ (US)

(72) Inventor: Emily H. Alexander, Alpine, TX (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 118 days.

(21) Appl. No.: 13/747,231

(22) Filed: Jan. 22, 2013

Related U.S. Application Data

(63) Continuation of application No. 11/056,511, filed on Feb. 11, 2005, now Pat. No. 8,374,887.

(51) Int. Cl.
*G06T 7/00* (2017.01)

(52) U.S. Cl.
CPC .................. *G06T 7/0012* (2013.01)

(58) Field of Classification Search
CPC ....................................................... G06Q 50/22
See application file for complete search history.

(56) References Cited

U.S. PATENT DOCUMENTS

| | | |
|---|---|---|
| 3,453,422 A | 7/1969 | Susor |
| 3,584,204 A | 6/1971 | Susor |
| 3,587,856 A | 6/1971 | Lemelson |
| 3,627,423 A | 12/1971 | Knapp |

(Continued)

FOREIGN PATENT DOCUMENTS

| | | |
|---|---|---|
| CA | 2477259 A1 | 9/2003 |
| GB | 2379037 A | 2/2003 |

(Continued)

OTHER PUBLICATIONS

Texas Administrative Code. Title 22. Examining Boards, 2004. (Year: 2004).*

(Continued)

*Primary Examiner* — Fonya M Long
*Assistant Examiner* — Kristine K Rapillo
(74) *Attorney, Agent, or Firm* — The Webb Law Firm

(57) ABSTRACT

A system and method for remotely supervising and verifying pharmacy functions performed by a non-pharmacist at an institutional pharmacy. The institutional pharmacy and a remotely located pharmacist are linked via wired and/or wireless telecommunication systems in a manner that enables the pharmacist to remotely supervise and verify the correct performance of pharmacy functions by non-pharmacist personnel. Images of the pharmacy work performed may be captured using any of a number of types image capture devices. Captured images and corresponding documentation may be transmitted from institutional pharmacy to the remotely located pharmacist, either directly or via a web site accessible to both. After verifying that the pharmacy work was correctly performed, the remote pharmacist may provide the institutional pharmacy with an initialed copy the captured image(s), or other documentation, indicating such verification. Receiving the pharmacist's verification may authorize the non-pharmacist to further process the work.

17 Claims, 9 Drawing Sheets

(56) References Cited

U.S. PATENT DOCUMENTS

| | | | |
|---|---|---|---|
| 3,734,286 A | | 5/1973 | Simjian |
| 3,914,058 A | | 10/1975 | Knapp et al. |
| 3,965,340 A | | 6/1976 | Renner et al. |
| 3,966,332 A | | 6/1976 | Knapp et al. |
| 4,017,157 A | | 4/1977 | van Riet |
| 4,063,823 A | | 12/1977 | Grat |
| 4,087,184 A | | 5/1978 | Knapp et al. |
| 4,165,633 A | | 8/1979 | Raisanen |
| 4,277,089 A | | 7/1981 | Lockhart |
| 4,469,146 A | | 9/1984 | Campbell et al. |
| 4,476,381 A | | 10/1984 | Rubin |
| 4,549,205 A | | 10/1985 | Misaki et al. |
| 4,628,193 A | | 12/1986 | Blum |
| 4,653,010 A | † | 3/1987 | Figler |
| 4,655,026 A | | 4/1987 | Wigoda |
| 4,676,650 A | | 6/1987 | Bjorndal et al. |
| 4,676,776 A | | 6/1987 | Howson |
| 4,695,954 A | | 9/1987 | Rose et al. |
| 4,733,363 A | | 3/1988 | Yamada et al. |
| 4,790,118 A | | 12/1988 | Chilcoate |
| 4,804,273 A | | 2/1989 | Tondello et al. |
| 4,810,243 A | | 3/1989 | Howson |
| 4,823,982 A | | 4/1989 | Aten et al. |
| 4,835,372 A | | 5/1989 | Gombrich et al. |
| 4,839,675 A | | 6/1989 | Owen |
| 4,853,521 A | | 8/1989 | Claeys et al. |
| 4,857,716 A | | 8/1989 | Gombrich et al. |
| 4,860,899 A | | 8/1989 | McKee |
| 4,874,764 A | | 10/1989 | Ueda et al. |
| 4,879,650 A | | 11/1989 | Kurimoto et al. |
| 4,918,604 A | | 4/1990 | Baum |
| 4,972,657 A | | 11/1990 | McKee |
| 5,031,642 A | | 7/1991 | Nosek |
| 5,038,839 A | | 8/1991 | Morimoto et al. |
| 5,072,798 A | | 12/1991 | Franklin |
| 5,088,981 A | | 2/1992 | Howson et al. |
| 5,094,786 A | | 3/1992 | Nagashima et al. |
| 5,153,827 A | | 10/1992 | Coutre et al. |
| 5,182,707 A | | 1/1993 | Cooper et al. |
| 5,261,546 A | | 11/1993 | van der Grift |
| 5,272,318 A | | 12/1993 | Gorman |
| 5,317,506 A | | 5/1994 | Coutre et al. |
| 5,328,208 A | | 7/1994 | Garrison |
| 5,337,919 A | | 8/1994 | Spaulding et al. |
| 5,341,077 A | | 8/1994 | Chen et al. |
| 5,341,854 A | | 8/1994 | Zezulka et al. |
| 5,344,043 A | * | 9/1994 | Moulding et al. .............. 221/71 |
| 5,348,061 A | | 9/1994 | Riley et al. |
| 5,365,343 A | | 11/1994 | Knapp |
| 5,390,796 A | | 2/1995 | Kerfoot, Jr. |
| 5,395,174 A | | 3/1995 | Koch et al. |
| 5,401,059 A | | 3/1995 | Ferrario |
| 5,404,227 A | | 4/1995 | Sumita et al. |
| 5,405,048 A | | 4/1995 | Rogers et al. |
| 5,416,706 A | | 5/1995 | Hagenbuch |
| 5,442,146 A | | 8/1995 | Bell et al. |
| 5,444,480 A | | 8/1995 | Sumita |
| 5,444,539 A | | 8/1995 | van der Grift |
| 5,468,110 A | | 11/1995 | McDonald et al. |
| 5,480,062 A | | 1/1996 | Rogers et al. |
| 5,502,944 A | | 4/1996 | Kraft et al. |
| 5,508,499 A | | 4/1996 | Ferrario |
| 5,523,560 A | | 6/1996 | Manique et al. |
| 5,568,262 A | | 10/1996 | LaChapelle et al. |
| 5,593,267 A | | 1/1997 | McDonald et al. |
| 5,597,995 A | | 1/1997 | Williams et al. |
| 5,601,314 A | | 2/1997 | Burns et al. |
| 5,643,212 A | | 7/1997 | Coutre et al. |
| 5,651,775 A | | 7/1997 | Walker et al. |
| 5,713,485 A | | 2/1998 | Liff et al. |
| 5,719,679 A | | 2/1998 | Shimizu et al. |
| 5,720,154 A | | 2/1998 | Lasher et al. |
| 5,721,433 A | | 2/1998 | Kosaka |
| 5,753,868 A | | 5/1998 | Diem |
| 5,758,095 A | | 5/1998 | Albaum et al. |
| 5,780,778 A | | 7/1998 | Schwartz et al. |
| 5,781,442 A | | 7/1998 | Engleson et al. |
| 5,797,515 A | * | 8/1998 | Liff et al. .......................... 221/2 |
| 5,833,866 A | | 11/1998 | Brown |
| 5,841,077 A | | 11/1998 | Kolaci |
| 5,841,541 A | | 11/1998 | Dlugos |
| 5,907,493 A | | 5/1999 | Boyer et al. |
| 5,940,176 A | | 8/1999 | Knapp |
| 5,963,136 A | | 10/1999 | O'Brien |
| 5,966,457 A | | 10/1999 | Lemelson |
| 5,969,317 A | | 10/1999 | Espy et al. |
| 5,979,512 A | | 11/1999 | McGregor et al. |
| 5,990,422 A | | 11/1999 | Komori et al. |
| 6,000,828 A | | 12/1999 | Leet |
| 6,005,959 A | | 12/1999 | Mohan et al. |
| 6,006,828 A | | 12/1999 | Kluth et al. |
| 6,068,156 A | | 5/2000 | Liff et al. |
| 6,088,527 A | | 7/2000 | Rybczynski |
| 6,113,578 A | | 9/2000 | Brown |
| 6,181,982 B1 | | 1/2001 | Yuyama et al. |
| 6,202,923 B1 | | 3/2001 | Boyer et al. |
| 6,234,964 B1 | * | 5/2001 | Iliff ............................... 600/300 |
| 6,260,023 B1 | | 7/2001 | Seevers et al. |
| 6,330,491 B1 | | 12/2001 | Lion |
| 6,347,486 B1 | | 2/2002 | Badillet |
| 6,364,517 B1 | | 4/2002 | Yuyama et al. |
| 6,384,348 B1 | | 5/2002 | Naga et al. |
| 6,438,451 B1 | | 8/2002 | Lion |
| 6,466,879 B1 | | 10/2002 | Cantu et al. |
| 6,473,169 B1 | | 10/2002 | Dawley et al. |
| 6,535,637 B1 | | 3/2003 | Wootton et al. |
| 6,542,902 B2 | | 4/2003 | Dulong et al. |
| 6,564,121 B1 | | 5/2003 | Wallace et al. |
| 6,574,580 B2 | | 6/2003 | Hamilton |
| 6,581,798 B2 | † | 6/2003 | Liff |
| 6,605,784 B2 | | 8/2003 | Eigenmann et al. |
| 6,694,334 B2 | | 2/2004 | DuLong et al. |
| 6,711,460 B1 | * | 3/2004 | Reese ................... G06Q 40/08 |
| | | | 700/216 |
| 6,731,324 B2 | | 5/2004 | Levy |
| 6,738,723 B2 | | 5/2004 | Hamilton |
| 6,771,369 B2 | | 8/2004 | Rzasa et al. |
| 6,775,602 B2 | | 8/2004 | Gordon, Jr. et al. |
| 6,781,689 B2 | | 8/2004 | Chiba |
| 6,810,355 B1 | | 10/2004 | Kreidler et al. |
| 6,813,473 B1 | | 11/2004 | Bruker |
| 6,814,255 B2 | | 11/2004 | Liff et al. |
| 6,816,625 B2 | | 11/2004 | Lewis, Jr. et al. |
| 6,873,725 B2 | | 3/2005 | Xu |
| 6,877,530 B2 | | 4/2005 | Osborne et al. |
| 6,915,823 B2 | | 7/2005 | Osborne et al. |
| 6,920,094 B2 | | 7/2005 | Komaki |
| 6,922,652 B2 | | 7/2005 | Edwards et al. |
| 6,937,339 B2 | | 8/2005 | Yamazaki et al. |
| 6,970,094 B2 | | 11/2005 | Yamashita et al. |
| 6,975,924 B2 | | 12/2005 | Kircher et al. |
| 6,995,664 B1 | | 2/2006 | Darling |
| 7,006,893 B2 | | 2/2006 | Hart et al. |
| 7,015,806 B2 | | 3/2006 | Naidoo et al. |
| 7,017,622 B2 | | 3/2006 | Osborne et al. |
| 7,017,623 B2 | | 3/2006 | Tribble et al. |
| 7,028,723 B1 | | 4/2006 | Alouani et al. |
| 7,070,097 B2 | | 7/2006 | Blanford et al. |
| 7,096,212 B2 | | 8/2006 | Tribble et al. |
| 7,107,106 B2 | | 9/2006 | Engelson et al. |
| 7,117,902 B2 | | 10/2006 | Osborne |
| 7,128,105 B2 | | 10/2006 | Tribble et al. |
| 7,163,035 B2 | | 1/2007 | Khan et al. |
| 7,164,336 B2 | | 1/2007 | Rausch et al. |
| 7,173,197 B1 | | 2/2007 | Kasperek |
| 7,194,336 B2 | | 3/2007 | DiGianfilippo et al. |
| 7,209,891 B1 | | 4/2007 | Addy et al. |
| 7,230,529 B2 | | 6/2007 | Ketcherside, Jr. et al. |
| 7,240,699 B2 | | 7/2007 | Osborne et al. |
| 7,262,847 B2 | | 8/2007 | Goodall et al. |
| 7,286,997 B2 | | 10/2007 | Spector et al. |
| 7,297,108 B2 | | 11/2007 | Iliff |
| 7,310,143 B2 | | 12/2007 | Budd |
| 7,317,967 B2 | | 1/2008 | DiGianfilippo et al. |

(56) References Cited

U.S. PATENT DOCUMENTS

| | | | |
|---|---|---|---|
| 7,343,224 B2 | 3/2008 | DiGianfilippo et al. | |
| 7,343,943 B2 | 3/2008 | Khan et al. | |
| 7,376,934 B2 | 5/2008 | Steinrisser et al. | |
| 7,391,515 B2 | 6/2008 | Budd et al. | |
| 7,427,002 B2 | 9/2008 | Liff et al. | |
| 7,457,685 B2 | 11/2008 | D'Silva | |
| 7,478,513 B2 | 1/2009 | Baldwin | |
| 7,493,263 B2 | 2/2009 | Helmus et al. | |
| 7,499,581 B2 | 3/2009 | Tribble et al. | |
| 7,530,497 B2 | 5/2009 | Knowles et al. | |
| 7,555,557 B2 | 6/2009 | Bradley et al. | |
| 7,560,720 B2 | 7/2009 | Voigt et al. | |
| 7,581,953 B2 | 9/2009 | Lehmann et al. | |
| 7,620,479 B2 | 11/2009 | Kircher et al. | |
| 7,620,563 B2 | 11/2009 | Tornaquindici | |
| 7,620,568 B1 | 11/2009 | Parker-Malchak | |
| 7,631,475 B2 | 12/2009 | Baldwin et al. | |
| 7,636,718 B1 | 12/2009 | Steen et al. | |
| 7,651,664 B2 | 1/2010 | Appoldt et al. | |
| 7,698,019 B2 | 4/2010 | Moncrief et al. | |
| 7,706,915 B2 | 4/2010 | Mohapatra et al. | |
| 7,753,085 B2 | 7/2010 | Tribble et al. | |
| 7,771,659 B2 | 8/2010 | Ziegler | |
| 7,831,447 B2 | 11/2010 | Schuman | |
| 7,847,970 B1 | 12/2010 | McGrady | |
| 7,860,583 B2 | 12/2010 | Condurso et al. | |
| 7,873,435 B2 | 1/2011 | Yuyama et al. | |
| 7,927,313 B2 | 4/2011 | Stewart et al. | |
| 7,930,364 B2 | 4/2011 | Ramaswamy et al. | |
| 7,937,290 B2 | 5/2011 | Bahir | |
| 7,941,915 B2 | 5/2011 | Yuyama et al. | |
| 7,956,894 B2 | 6/2011 | Akers et al. | |
| 7,995,831 B2 | 8/2011 | Eller et al. | |
| 8,140,349 B2 | 3/2012 | Hanson et al. | |
| 8,219,413 B2 | 7/2012 | Martinez et al. | |
| 8,220,503 B2 | 7/2012 | Tribble et al. | |
| 8,224,483 B1 | 7/2012 | Ansari et al. | |
| 8,234,128 B2 | 7/2012 | Martucci et al. | |
| 8,266,878 B2 | 9/2012 | Luciano, Jr. et al. | |
| 8,280,549 B2 | 10/2012 | Liff et al. | |
| 8,295,582 B2 | 10/2012 | Eller et al. | |
| 8,489,425 B2 | 7/2013 | Moncrief et al. | |
| 8,571,297 B2 | 10/2013 | Eller et al. | |
| 8,571,881 B2 | 10/2013 | Rousso et al. | |
| 8,571,886 B2 | 10/2013 | Chudy et al. | |
| 2002/0057339 A1 | 5/2002 | Shoenfeld | |
| 2002/0067411 A1 | 6/2002 | Thompson et al. | |
| 2002/0100762 A1 | 8/2002 | Liff et al. | |
| 2002/0139394 A1 | 10/2002 | Bronson | |
| 2003/0050731 A1* | 3/2003 | Rosenblum | 700/232 |
| 2003/0050802 A1 | 3/2003 | Jay et al. | |
| 2003/0074223 A1 | 4/2003 | Hickle et al. | |
| 2003/0078849 A1 | 4/2003 | Snyder | |
| 2003/0105555 A1* | 6/2003 | Lunak et al. | 700/237 |
| 2003/0107654 A1 | 6/2003 | Ohmura | |
| 2003/0136590 A1 | 7/2003 | Gluvakov | |
| 2003/0139701 A1 | 7/2003 | White et al. | |
| 2003/0140928 A1 | 7/2003 | Bui et al. | |
| 2003/0144878 A1 | 7/2003 | Wilkes et al. | |
| 2003/0158508 A1* | 8/2003 | DiGianfilippo et al. | 604/4.01 |
| 2003/0179287 A1 | 9/2003 | Kozic et al. | |
| 2003/0204357 A1 | 10/2003 | Hamilton | |
| 2004/0017475 A1 | 1/2004 | Akers et al. | |
| 2004/0076318 A1 | 4/2004 | Faeldt et al. | |
| 2004/0143459 A1 | 7/2004 | Engleson et al. | |
| 2004/0150815 A1 | 8/2004 | Sones et al. | |
| 2004/0172289 A1* | 9/2004 | Kozic et al. | 705/2 |
| 2004/0193454 A1 | 9/2004 | Foote et al. | |
| 2004/0204954 A1 | 10/2004 | Lacko | |
| 2004/0225528 A1 | 11/2004 | Brock | |
| 2005/0080651 A1† | 4/2005 | Morrison | |
| 2005/0086008 A1 | 4/2005 | DiGianfilippo et al. | |
| 2005/0130173 A1 | 6/2005 | Leamon et al. | |
| 2005/0197930 A1 | 9/2005 | Polarine | |
| 2006/0080041 A1 | 4/2006 | Anderson et al. | |
| 2006/0080177 A1 | 4/2006 | Walter et al. | |
| 2006/0106647 A1 | 5/2006 | Brummel et al. | |
| 2006/0136260 A1 | 6/2006 | Ash et al. | |
| 2006/0136261 A1 | 6/2006 | Ash et al. | |
| 2006/0136268 A1 | 6/2006 | Ash et al. | |
| 2006/0173714 A1 | 8/2006 | Grotzinger, Jr. | |
| 2006/0200369 A1 | 9/2006 | Batch et al. | |
| 2007/0021929 A1 | 1/2007 | Lemo et al. | |
| 2007/0228172 A1 | 10/2007 | Knowles et al. | |
| 2008/0045811 A1 | 2/2008 | Iliff | |
| 2008/0047760 A1 | 2/2008 | Georgitsis | |
| 2008/0052120 A1 | 2/2008 | Iliff | |
| 2008/0052121 A1 | 2/2008 | Iliff | |
| 2008/0052122 A1 | 2/2008 | Iliff | |
| 2008/0052123 A1 | 2/2008 | Iliff | |
| 2008/0052130 A1 | 2/2008 | Iliff | |
| 2008/0052132 A1 | 2/2008 | Iliff | |
| 2008/0105468 A1 | 5/2008 | Ragazzini et al. | |
| 2008/0125897 A1 | 5/2008 | DiGianfilippo et al. | |
| 2008/0312861 A1 | 12/2008 | Casto et al. | |
| 2009/0202108 A1 | 8/2009 | Faeldt et al. | |
| 2010/0057264 A1 | 3/2010 | Kircher et al. | |
| 2011/0202366 A1 | 8/2011 | Akers et al. | |

FOREIGN PATENT DOCUMENTS

| | | |
|---|---|---|
| WO | 8700659 A1 | 1/1987 |
| WO | 03040980 A1 | 5/2003 |

OTHER PUBLICATIONS

Canadian Pharmacists Association, Environmental Scan of Pharmacy Technicians, Sep. 2001 pp. 1-16.

Yahoo Mail, Oct. 1, 2002 pp. 1-3.

CardinalCSC After hours pharmacy service, 2003 pp. 1-3.

Sandra C. Woodall, Pharm.D., "Remote Order Entry and Video Verification," Aug. 2004, Joint Commission on Accreditation of Healthcare Organizations, vol. 30 No. 8, pp. 442-447.

Joseph Tracy "A Guide to Getting Started in Telemedicine," Telemedicine Technical Assistance Documents, Chapter 10, 2004 pp. 206-240.

"Regulatory Compliance News Summary; now includes global pharmaceutical regulatory news," Aug. 24, 2004, Regulatory Compliance News Summary from First Consulting Group, pp. 1-7.

U.S. Appl. No. 11/056,511, filed Feb. 11 2005, Emily H. Alexander.

Office Action from U.S. Appl. No. 11/056,511 dated Apr. 8 2008, Emily H. Alexander pp. 1-12.

Office Action from U.S. Appl. No. 11/056,511 dated Oct. 16 2008, Emily H. Alexander pp. 1-17.

Office Action from U.S. Appl. No. 11/056,511 dated Apr. 13 2009, Emily H. Alexander pp. 1-15.

Office Action from U.S. Appl. No. 11/056,511 dated Feb. 3 2010, Emily H. Alexander pp. 1-15.

Notice of Allowance from U.S. Appl. No. 11/056,511 dated Dec. 24 2012, Emily H. Alexander pp. 1-16.

U.S. Appl. No. 13/097,575, filed Apr. 29 2011, Emily H. Alexander.

G. Dennis Clifton et al. Provision of pharmacy services to underserved populations via remote dispensing and two-way videoconferencing. Am. J. Health-Syst. Pharm, vol. 60, pp. 2577-2582. Dec. 15, 2003.

Langham. Winston Salem Health Care Pharmacy: Taking Automation to New Levels. Insight, Oct. 2002, pp. 3-5.

Peterson and Anderson. Telepharmacy. In Tracy (ed.) A Guide to Getting Started in Telemedicine. pp. 206-240 (2004).

David Angaran. Telemedicine and telepharmacy: Current status and future implications. Am. J. Health-Syst. Pharm, vol. 56(14). Jul. 15, 1999.

James Cabral Jr. and Yongmin Kim. Multimedia Systems for Telemedicine and Their Communications Requirements. IEEE Communications Magazine, Jul. 1996, pp. 20-27.

Carol Ukens. Pharmacist shortage boosts telepharmacy. Drug Topics, vol. 146(11), p. 53. Jun. 3, 2002.

Eric S. Kastango and Brian D. Bradshaw. USP chapter 797: Establishing a practice standard for compounding sterile preparations in pharmacy. Am. J. Health-Syst. Pharm, vol. 61, pp. 1928-1938. 2004.

(56) References Cited

OTHER PUBLICATIONS

Ahuva Lustig. Medication error prevention by pharmacists—An Israeli solution. Pharm World Sci, vol. 22(1), pp. 21-25. 2000.
Aisha M. Morris et al. National survey of quality assurance activities for pharmacy-compounded sterile preparations. Am. J. Health-Syst. Pharm, vol. 60, pp. 2567-2576. Dec. 15, 2003.
Michael Rouse et al. White paper on pharmacy technicians 2002: Needed changes can no longer wait. Am. J. Health-Syst. Pharm, vol. 60, pp. 37-51. 2003.
Donna Young. Loan repayments help pharmacists provide care in medically underserved areas. Am. J. Health-Syst. Pharm, vol. 60 pp. 2186-2188. Nov. 1, 2003.
Rich Muller. Electronic Prescribing—What You Need to Know. Insight, pp. 10-12. Apr. 2002.
Christopher A. Keeys. Providing nighttime pharmaceutical services through telepharmacy. Am. J. Health-Syst. Pharm., vol. 59, pp. 716-721. Apr. 15, 2002.
Lisa Nissen and Susan Tett. Can telepharmacy provide pharmacy services in the bush? J. of Telemedicine & Telecare, vol. 9, pp. 39-41. 2003.
Napoli M et al. Picture archiving and communication in radiology. Rays, vol. 28(1). Jan.-Mar. 2003. (Abstract only).
Rural Hospital Joins the Big Leagues with the Power of a Kodak PACS/Enterprise Information Management (EIM) Solution. Health Group, 2005.
Rich Muller. Make Your Next Move NRx QS/1's Premium Pharmacy Software. Insight, pp. 12-15. Jul. 2003.
Frady. What's New in RxCare Plus 17.2. Insight, p. 14. Apr. 2002.
Luann Dart. Digital Doses: Telepharmacies save people in small towns and rural areas from having to drive hundreds of miles to fill a prescription. Rural Electric, pp. 28-30. Jan. 2005.
Luann Dart. Telepharmacy project offers a dose of technology. North Dakota Living, pp. 10-11. Nov. 2003.
David Kosub. Device allows pharmacy care in remote areas. Pharmacy Practice, vol. 20(10), pp. 12-13. Oct. 2004.
Michelle M. Casey et al. Access to Rural Pharmacy Services in Minnesota, North Dakota, and South Dakota. Jul. 2001.
North Dakota State Board of Pharmacy Practice Act 2003.
Charles F. Seifert et al. The Training of a Telepharmacist: Addressing the Needs of Rural West Texas. Am. J. of Pharm. Ed., vol. 68(3). Jul. 16, 2004.
Natale Ghent. Pharmacists go digital to fight shortage. Pharmacy Practice, vol. 20(10). Nov. 2004.
Robert D. Wills. Drug Images and Drug Imprints: Delivering Tools for Accuracy in Your Pharmacy. Insight, Apr. 2004.
Liz Parks. ATM-Style Drug Dispensers Taking Hold in Areas With Limited Pharmacist Services. Pharmacy Practice News Source, vol. 31:01. Jan. 2004.
Eileen Koutnik. Pharmacy Times, The Pharmacy of Tomorrow. Aug. 1, 2003.
Kathryn Hix. Outpatient Pharmacies 'Booming': An Inside Look at the Growth of an Industry. Insight, Apr. 2004.
Dan Scheraga. Tech firms answer chain pharmacy's call for productivity. Drug Store News, pp. 31-32. Dec. 15, 2003.
Liz Parks. Using central-fill to maximize dispensing. Drug Store News, vol. 23(11). pp. 51, 75. Aug. 20, 2001.
Helmut Hoerner. Pharmweb Internet Posting, Jan. 1999.
Title 22, Part 15, Chapter 291, Rules 20, 36, and 71-74 of the Texas Administrative code Feb. 2004.
Phillips. "Telepharmacy at Texas Tech." presented Apr. 2003.
United States Phamacopeia, Chapter 797. Jan. 2004.
Petition for Inter Partes Review of U.S. Pat. No. 8,374,887.
Bynum. The effect of telepharmacy counseling on metered-dose inhaler technique among adolescents with asthma in rural Arkansas. Telemedicine J. vol. 7(3), pp. 207-218. 2001.

Felkey. Tools for interactive telepharmacy. Computer Talk for the Pharmacist, vol. 21(1), Jan./Feb. 2001. pp. 43-45.
Felkey. Integrating technology at the point of care. Insight, Jan. 2004. pp. 8-10.
Halverson. Rural Wisconsin Health Cooperative: Virtual Private Network Feasibility and Design Study. Sep. 2001.
Chains covet customized pharmacy integration. Drug Store News, Aug. 18, 2003, pp. 73-74, 83.
ScriptPro. SP 200 with Collating Control Center Robotic Prescription Dispensing System. Available online as of Feb. 13, 2004.
ScriptPro. SP Automation Center 200. Available online as of Feb. 10, 2004.
ScriptPro. SP 2000 Robotic Dispensing system. Available online as of Feb. 13, 2004.
"The North Dakota Telepharmacy Project: Restoring and Retaining Pharmacy Services in Rural Communities", Charles D. Peterson and Howard C. Anderson Jr., J Pharm Technol, Jan./Feb. 2004, pp. 28-39.
"Chapter 61-02-08 Telepharmacy Rules", Dakota Legislative Assembly, accessed Aug. 26, 2014, 1 page.
"Article 61-07 Hospital Pharmacy", Dakota Legislative Assembly, Oct. 2012, pp. 1-14.
Final Written Decision, Inter Partes Review of U.S. Pat. No. 8,374,887, Jul. 11, 2016.
Order on Motion for Summery Judgment of U.S. Pat. No. 8,374,887 in WDTX Case No. 14-cv-00222, published on Aug. 3, 2015 via CM/ECF.†
Decision Instituting IPR2015-00883 of U.S. Pat. No. 8,374,887, published on Aug. 13, 2015 via PRPS.†
Petition for Inter Partes Review of U.S. Pat. No. 8,374,887, published in IPR2015-00883 on Mar. 16, 2015 via PRPS.†
Patent Owner Preliminary Response in IPR2015-00883, published on Jun. 12, 2015 via PRPS.†
Patent Owner Response in IPR2015-00883, published on Oct. 27, 2015 via PRPS.†
Excerpts from 22 Texas Administrative Code §§ 291.20, 291.36, and 291.71-291.74, published by Thompson West as of Dec. 31, 2003.†
North Dakota Telepharmacy Project Restoring and Retaining Pharmacy Services in Rural Communities, published in the Journal of Pharmacy Technology by Feb. 13, 2004.†
Seifert, Charles, The Trebling of a Telephermactst Addressing the Needs of Rural West Texas, published in the American Journal of Pharmaceutical Education by at least Jul. 16, 2004.†
Excerpts from United States Pharmacopeia (Standards), published on Dec. 19, 2003.†
Declaration of Mr. Brian T. Hart, published as Ex. 1003 in IPR2015-00883 on Mar. 16, 2015 via PRPS.†
Declaration of Dr. Wayne H. Grant, published as Ex. 1004 in IPR2015-00883 on Mar. 16, 2015 via PRPS.†
Final Written Decision in IPR2015-00883, published on Jul. 11, 2016 via PRPS.†
Notice of Entry of Judgment Without Opinion, published on May 9, 2016 via ECF.†
Petitioner's Reply to Patent Owner's Response in IPR2015-00883, published on Jan. 11, 2016 via PRPS.†
Deposition of Charles F. Seifert, PharmD published as Ex. 1030 in IPR2015-00883 on Jan. 11, 2016 via PRPS.†
Deposition of Diane B. Ginsburg, Ph.D. published as Ex. 1031 in IPR2015-00883 on Jan. 11, 2016 via PRPS.†
Texas Administrative Code, Title 22, § 291.23, Pilot Project Authorization in effect on Feb. 1, 2004.†
Deposition of Brian T. Hart published as Ex. 1031 in IPR2015-00883 on Jan. 11, 2016 via PRPS.†
Record of Oral Hearing Held on Apr. 6, 2016 in IPR2015-00883, published on May 17, 2016 via PRPS.†

\* cited by examiner
† cited by third party

SYSTEM AND METHOD FOR REMOTELY SUPERVISING AND VERIFYING PHARMACY FUNCTIONS

This application is a continuation of U.S. application Ser. No. 11/056,511, filed Feb. 11, 2005, which is hereby incorporated by reference in its entirety.

BACKGROUND OF THE INVENTION

Field of the Invention

The present disclosure relates to pharmacy services, and more specifically, to a method and a system for remotely supervising and verifying technical pharmacy functions performed by a non-pharmacist located in an institutional pharmacy

Description of the Related Art

A pharmacist's scope of practice in institutions, such as hospitals or correctional facilities, includes preparing, packaging, compounding, and labeling medication, compounding sterile products, as well as other medication related activities. Many technical functions involving the preparation and distribution of drugs may be performed in the pharmacy by non-pharmacist personnel, usually a pharmacy technician or licensed nurse. When a non-pharmacist performs such functions a pharmacist must generally verify their work.

When a non-pharmacist performs technical pharmacy functions, such as pursuant to a written medication order, a pharmacist typically verifies the work, in part, by comparing it to either a copy of the original medication order, or a medication order previously entered into the patient's medication profile. The pharmacist also supervises the work of the non-pharmacist, and verifies that the medication product has been correctly and accurately prepared, labeled, compounded, and/or packaged. When a non-pharmacist performs technical pharmacy functions involving prepackaging, labeling, bulk compounding, or batch preparation of medications that will serve as stock medication in the pharmacy department, a pharmacist must generally verify the work in much the same manner. The pharmacist must supervise the work of the non-pharmacist to verify that the medication has been correctly and accurately prepared, labeled, compounded, and/or packaged.

The majority of institutional pharmacies do not have pharmacists on duty 24 hours, 7 day per week, yet patients frequently require medications that are only available in the pharmacy department of an institution when no pharmacist is on duty. Under such circumstances, no pharmacist can supervise or verify the performance of the pharmacy functions performed. As a result, patients may receive medication that has been prepared, packaged, compounded, and labeled without being first verified by a pharmacist. In some cases, a pharmacist on duty later may retrospectively verify that the pharmacy work was performed correctly. For example, when it is necessary that a patient receive a new order for a medication that is only available from the pharmacy after regular pharmacy hours, a nurse, or other non-pharmacist personnel, may enter the pharmacy to obtain the medication for the patient. The patient will have already received the medication by the time a pharmacist returns to duty. Upon the pharmacist's return, he must verify that the nurse used the correct medication, in the correct dose and dosage form, as well as verify documentation regarding the patient for whom the medication was removed, the person removing the medication, and when the removal occurred. An error may thus be discovered, but not prevented by the pharmacist.

Another example of sub-optimal medication safety that may result from lack of pharmacist availability is demonstrated when medication is removed from the pharmacy after hours in a multi-dose packaging form. While this practice increases the potential for medication errors, the lack of pharmacist availability may necessitate it, as follows. If a multi-dose stock bottle of medication was purchased and received in the pharmacy when a pharmacist is not on duty, the unit dose packaging process must wait for the pharmacist's supervision and verification. In this case, if a patient requires this same medication before a pharmacist is on duty, regulations may require that the entire stock bottle be removed from the pharmacy in order for the patient to receive a dose.

SUMMARY

A system and method are described herein for providing certain pharmacy services to institutionalized patients at an institution where a live pharmacist is not available. The institutional pharmacy and a remotely located pharmacist are linked via wired or wireless telecommunication systems in a manner that enables the pharmacist to remotely supervise and verify that pharmacy functions are properly performed by non-pharmacist personnel. In order to facilitate remote supervision and verification, the pharmacist site(s), institutional pharmacy site(s), and a system website may be linked to one another via an Internet connection, virtual private network, or in general any wired or wireless link, so that information may be exchanged. For example, a pharmacist site and an institutional pharmacy site may be linked via an Internet connection, using telephone lines, wireless links, or a combination of wireless links and wired links. Additionally, the pharmacist site and the institutional pharmacy site may be linked to a system website via an Internet connection.

A pharmacist site may include a workstation with one or more monitors, Internet connectivity, printer, scanner, copier, telephone and facsimile machine, according to one embodiment. It may also include a local area network and additional workstations. An institutional pharmacy site may generally include an image capture device (e.g. a visual presenter or document viewer) linked to a workstation, which may be linked to a local area network. The local area network or workstation may be generally linked via an Internet connection, telephone lines, wireless links, or a combination of wireless links and wired links to other sites (e.g. a pharmacist site). The site typically also includes telephone lines, facsimile machine(s), and a printer.

The method and system for remotely supervising and verifying pharmacy functions may include using a image capture device located in the institutional pharmacy, linked to a computer system, to capture images of work performed by non-pharmacist personnel. The image(s) and corresponding documentation are transmitted from the institutional pharmacy to a remotely located computer system, where a pharmacist supervises and verifies the work, and subsequently authorizes non-pharmacist personnel to further process the work.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

Figure 1:
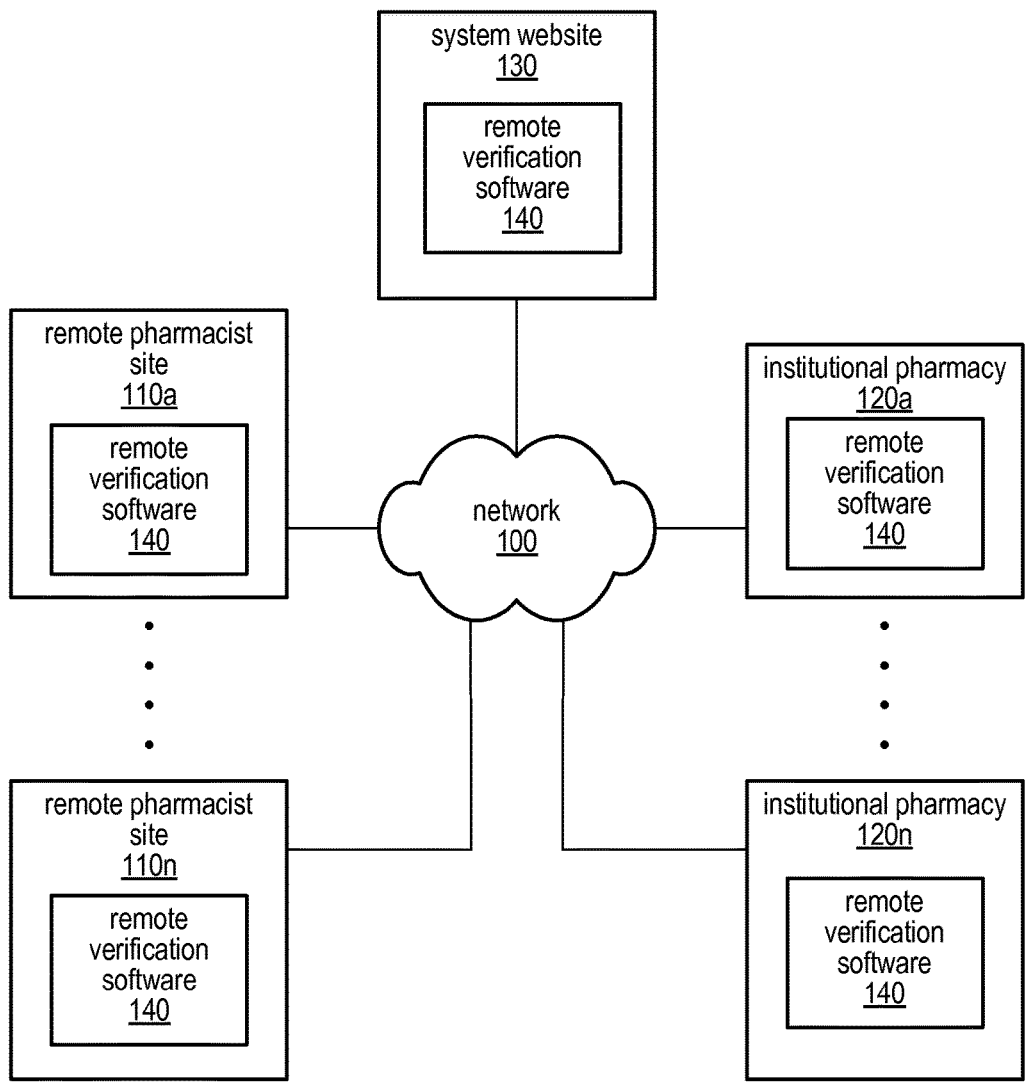
FIG. 1 illustrates, according to one embodiment, a block diagram of a networked environment suitable for implementing remote supervision and verification of pharmacy functions, as described herein.

Pharmacy functions performed by a non-pharmacist may be remotely supervised and verified by a remote pharmacist using a networked environment, such as illustrated by FIG. 1, according to some embodiments. Pharmacists at one or more remote pharmacist sites 110 may remotely supervise and verify pharmacy work tasks performed by non-pharmacists at one or more institutional pharmacies 120, according to some embodiments. Remotely supervised and verified pharmacy work tasks may include pharmacy functions performed pursuant to medication orders and may also include pharmacy functions not related to specific medication orders, according to various embodiments. In general, the term "pharmacy work task" as used herein may describe any pharmacy functions capable of being remotely supervised and verified by the methods and systems described herein, whether or not performed pursuant to a medication order.

As illustrated in FIG. 1, a remote pharmacist site may be communicably linked to one or more institutional pharmacies while located remotely from the institutional pharmacies. For instance, institutional pharmacy 120 and remote pharmacist site 110 may be located in different parts of the same building, in one embodiment. In other embodiments, however, institutional pharmacy 120 and remote pharmacist site 110 may be in different buildings of the same institution, in the same town, in different cities, counties, or states. In general, remote pharmacist site 110 and institutional pharmacy 120 may be located anywhere as long they can communicate with each other either directly or indirectly.

Remote pharmacist site 110 and institutional pharmacy 120 may communicate via any of various wired or wireless communication systems, according to various embodiments. For example, in one embodiment, they may communicate via email over the Internet. In another embodiment, they may communicate via a custom communication protocol configured for exchanging messages related to remotely supervising and verifying pharmacy functions, such as may be implemented by remote verification software 140, as will be discussed herein below. In yet another embodiment, remote pharmacist site 110 and institutional pharmacy 120 may communicate via a website or electronic bulletin board, such as system website 130, by uploading and downloading various documents, images and/or other information related to remotely supervising and verifying pharmacy functions. Additionally, remote pharmacist site 110 may communicate with a pharmacy order entry system or other software at institutional pharmacy 120 via an Internet connection, virtual private network, or any wired or wireless link, according to one embodiment. For example, a pharmacist at remote pharmacist site 110 may communicate with such an order entry system or other software at institutional pharmacy 120 in order to verify a patient's medication order.

As illustrated by FIG. 1, multiple remote pharmacist sites 110 may exist in the system at once, as well as multiple institutional pharmacy sites 120, according to some embodiments. A single remote pharmacist 110 may remotely supervise and verify pharmacy functions performed at more than one institutional pharmacy sites 120. Additionally, a pool of remote pharmacist sites 110 may work together to remotely supervise and verify pharmacy functions performed at multiple institutional pharmacy sites 120, in some embodiments. For example, a number of remote pharmacist sites 110 may each remotely supervise and verify pharmacy functions for any of a number of institutional pharmacy sites 120 on a rotational or as needed basis. For instance, in one embodiment, a pharmacist at remote pharmacist site 110 may check and/or verify images from one or more institutional pharmacy sites 120 randomly chosen out of a number of available institutional pharmacy sites 120. In another embodiment, a remote pharmacist site may remotely verify pharmacy functions performed at a number of institutional pharmacy sites on a first-come first-served basis in which the institutional pharmacies are serviced in the order they notified the remote pharmacist that images were available for verification.

According to some embodiments, pharmacy functions performed at institutional pharmacy 120 that may be remotely supervised and verified may include, but are not limited to:

1. Packaging, prepackaging and labeling unit and multiple dose packages.
2. Medication preparation, packaging, compounding or labeling pursuant to medication orders.
3. Compounding of sterile pharmaceuticals pursuant to medication orders.
4. Bulk compounding or batch preparation.

The terms prepackaging and packaging, as used herein, may refer to two different pharmacy functions. Prepackaging refers to the re-packaging and/or re-labeling quantities of drug products from a manufacturer's original commercial container, such as into a prescription container for dispensing. Packaging, on the other hand, refers to collecting one or more medications into a final package to be dispensed to the ultimate consumer. For example, packaging may refer to a technician selecting appropriate quantities of manufacturer's unit dosed products and/or prepackaged stocked medications necessary to fill a patient's admission orders. The technician may then package the selected medications into a bag with an affixed label indicating the patient for whom the medications were ordered. As with other pharmacy functions, the prepackaging and the final packaging of medications may be remotely supervised and verified by a pharmacist, as described herein.

Remote verification of pharmacy functions performed by non-pharmacists may additionally include, in some embodiments, one or more legally required in-progress checks. In general, remote pharmacist verification of pharmacy work performed by non-pharmacists may include supervision and/or verification of the pharmacy work in various stages of completion as well as verification of any and/or all results of the pharmacy work, according to various embodiments.

The Institutional Pharmacy Site:

An institutional pharmacy 120 may be a pharmacy located in an institution, such as a hospital or correctional facility. In general, institutional pharmacy 120 may be any pharmacy that cannot or does not have a pharmacist on site at all times. As illustrated in FIG. 1, an institutional pharmacy 120 may be linked to a system website 130 and/or one or more remote pharmacist site(s) 110 via any of a number of ways, such as over the Internet, a virtual private network, or, in general, any wired or wireless communication system configured to allow the exchange of information related to remote supervision and verification of pharmacy functions, as described herein. For instance, institutional pharmacy 120 may communicate with remote pharmacist site 110 over network 100, which may be the Internet in one embodiment. In other embodiments, institutional pharmacy 120 may communicate with remote pharmacist site 110 directly over a telecommunications system, such as the Public Switched Telephone Network (PSTN) or over a cellular or satellite telecommunications system.

In some embodiments, system website 130 may represent an electronic bulletin board, or other shared electronic data storage facility, to which images, documents, and/or other files may be posted, uploaded, or otherwise stored. Images uploaded or posted to a web site or bulletin board may be compressed, encrypted, or combined (either compressed or uncompressed) into a single file, according to various embodiments. For example, in one embodiment, captured images may be uploaded in an encrypted form and a key or password to decrypt the images may be provided to a remote pharmacist in a separate communication. Furthermore, system website 130 may require secure login credentials, such as a username and password, before allowing images to be uploaded or accessed. Alternatively, a public/private key encryption schema may be utilized to ensure the security of the captured images in some embodiments. For example, the captured images may be encrypted using the remote pharmacist's public encryption key and may be decrypted by the pharmacist using the pharmacist's private encryption key. Additionally, any of various forms of secure electronic communication may be utilized to transfer the captured images in some embodiments. For example, in one embodiment, one or more images of pharmacy work may be transferred to system website 130 via a secure http protocol, such as HTTPS. In yet other embodiments, captured images may be digitally signed using digital certificate technology. For instance, the images may be digitally signed using the institutional pharmacy's digital signature or certification which a remote pharmacist may verify using an appropriate digital certification authentication authority. As encryption, secure electronic communication, and digital signature and certificate technologies are well understood in the art, they are not discussed in detail herein.

Figure 2:
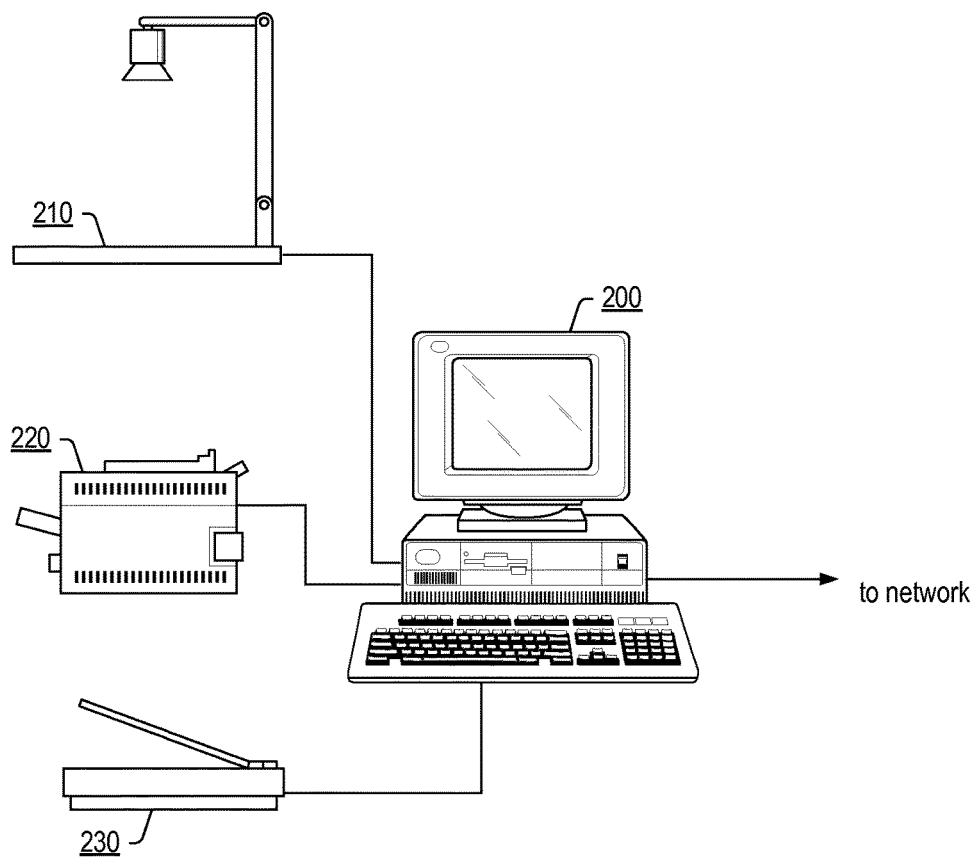
FIG. 2 illustrates one embodiment of an exemplary institutional pharmacy workstation.

Referring now to FIG. 2, which illustrates one embodiment of an institutional pharmacy workstation for implementing remote supervision and verification of pharmacy functions, as described herein. One or more workstations, such as illustrated in FIG. 2 may be located at institutional pharmacy 120, according to some embodiments. As illustrated by FIG. 2, such a workstation may include an image capture device capable of accommodating three-dimensional objects, such as image capture device 210, that may be coupled to a computer 200. An institutional pharmacy workstation may, in some embodiments, also include a printer 220, scanner 230, and may also have a telephone and a facsimile machine, not shown in FIG. 2.

Image capture device 210 may be any of a number of different types of image capture devices configured to capture still and/or video images or clips, according to various embodiments. For example, in one embodiment, image capture device 210 may be an off-the-shelf digital camera mounted appropriately to capture images of pharmacy work. In another embodiment, image capture device 210 may be a visual presenter, while in other embodiments, image capture device may be a web cam configured to capture still and/or video images or clips. In yet other embodiments, image capture device 210 may be a custom image capture device configured specifically for capturing images of pharmacy functions. The manner of capturing images with image capture device 210 may also vary from embodiment to embodiment. For instance, in one embodiment, image capture device 210 may be mounted above a pharmacy work area, while in other embodiments, image capture device 210 may be mounted proximate to an area specifically for arranging ingredients, materials, and/or documentation for pharmacy functions. In yet other embodiments, image capture device 210 may be a handheld image capture device capable of communicating, either directly or indirectly with computer 200.

When non-pharmacist personnel, such as pharmacy technicians and/or licensed nurses, perform pharmacy functions requiring the supervision and verification of a pharmacist, in the absence of an on-site pharmacist, the still image capture device can be used to capture one or more images of the pharmacy work performed. The captured images may, in some embodiments, include images of all work and documentation required to properly supervise and verify the correct and accurate preparation, labeling, compounding, prepackaging and/or packaging, of any pharmacy work performed. The captured images may also include any additional documentation required for record keeping purposes, in some embodiments. Multiple images may be captured for remote supervision and verification process as needed, according to some embodiments. For example, if all documentation and materials required for the pharmacy work do not fit in the view of image capture device 210, two or more images may be captured.

In some embodiments, multiple images may be uploaded together as a single post to a website or bulletin board, such as system website 130. For instance, in one embodiment, multiple images may be uploaded to a website or bulletin board as a single post and inclusion of multiple images in a single post may indicate all of the included images are part of a single pharmacy task that requires remote supervision and verification. Alternatively, in other embodiments, each of the captured images for a single pharmacy work task, whether for a medication order or other pharmacy work, may contain some indication that they are part of the same pharmacy work task. For example, in one embodiment, each related image could include a unique reference number associated with the pharmacy work task. Reference numbers may be included in captured images using a number of different techniques, according to various embodiments. For example, in one embodiment, a small piece of paper with a reference number printed on it may be in the view of image capture device 210 when each image is captured. In another embodiment, reference numbers may be overlayed on, inserted in, or otherwise graphically added to the captured images, such as by software in computer 200. In yet other embodiments, image capture device 210 may be configured to automatically graphically include, add, or overly reference numbers to captured images. An order identification number from a medication order may be included as a reference number in captured images, according to one embodiment. In other embodiments, reference numbers may be generated for each set of related images, such as by an order entry system for entering medication information into a patient's medication profile. In general, any type or sort of reference indicators, either alphanumeric or graphical, may be used to indicate related captured images.

Figure 3:
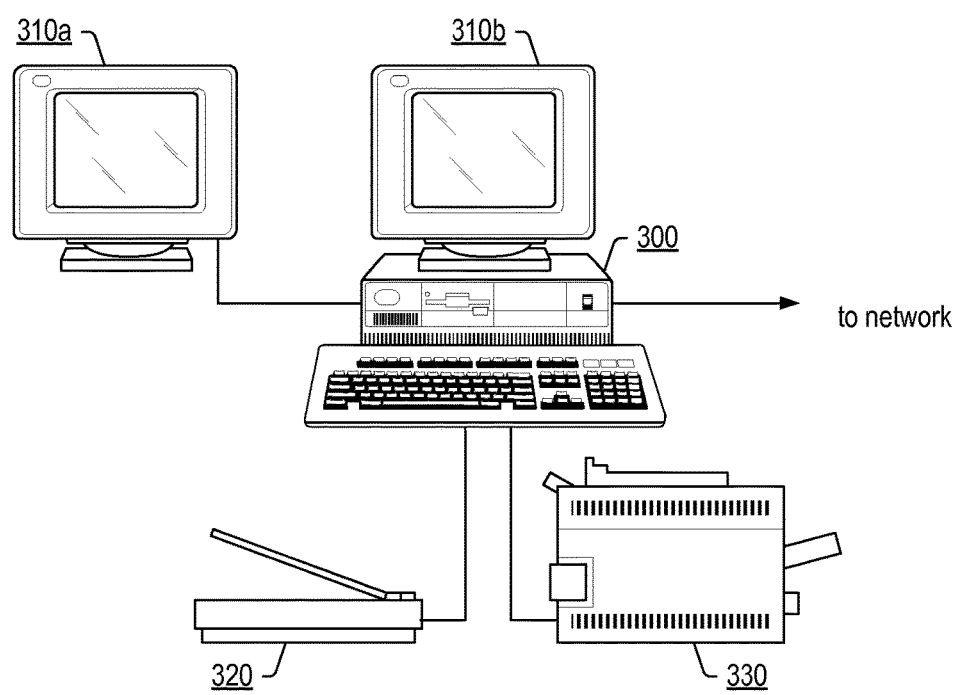
FIG. 3 illustrates one embodiment of an exemplary remote pharmacist workstation.

The Remote Pharmacist Site:

FIG. 3 illustrates an exemplary workstation used by a pharmacist at remote pharmacist site 110, according to some embodiments. A remote pharmacist workstation may include a computer 300 with one or more monitors, such as monitors 310a and 310b, allowing viewing captured images of pharmacy work performed as institutional pharmacy 120. According to some embodiments, a remote pharmacist workstation may include two monitors 310 coupled to computer 300 to allow simultaneous viewing of two images. A remote pharmacist workstation 110 may also have Internet connectivity for communicating with institutional pharmacy 120, according to one embodiment. A remote pharmacist workstation 110 may, in some embodiments, also include, but is not limited to, a scanner 320, a printer 330, telephone, fax machine, and/or a copier. A remote pharmacist workstation may communicate with one or more institutional pharmacies 120 and/or with system website 130 via an Internet connection, virtual private network, LAN, WAN, or in general any wired or wireless link, according to various embodiments.

In some embodiments, more than one pharmacist may be on duty at a single remote pharmacist site 110 and thus a remote pharmacist site 110 may include more than one remote pharmacist workstation. In such an embodiment, multiple remote pharmacist workstations may be linked via a local network, such as a LAN or WAN, and each workstation may be configured to communicate via an Internet connection provided by the local network.

Each remote pharmacist site 110 may have one or more pharmacist on duty, as well as other non-pharmacist support personnel, according to various embodiments. Any pharmacist that remotely supervises and/or verifies pharmacy functions performed by non-pharmacist personnel at institutional pharmacy 120 from a remote pharmacist site 110 may be required to have licensure to practice pharmacy in the state in which the institutional pharmacy 120 being serviced is located, in accordance with state laws. As noted above, a pharmacy functions performed at institutional pharmacy 120 may be remotely supervised and verified by a pharmacist at a remote pharmacist site remotely located from institutional pharmacies 120, according to various embodiments. In general a remote pharmacist site 110 may be in any location, including another pharmacy, but generally would not be located in the same facility as the institutional pharmacy it is serving. Although, in certain embodiments, a pharmacist located in one part of a large institution may remotely supervise and verify pharmacy functions performed in multiple institutional pharmacies 120 located in other parts of the same institution. For example, a large institution may include one or more different pharmacy stock areas, or satellite pharmacies, that operate under a single pharmacy license and in some embodiments pharmacy functions performed at satellite pharmacies may be remotely supervised and verified by a remote pharmacist either on duty in a main pharmacy, a different one of the satellite pharmacies, or located offsite. Alternatively, in other embodiments, a large institution may include more than one pharmacy and pharmacy functions performed at one pharmacy may be remotely supervised and verified by a pharmacist at a different one of the pharmacies.

A remote pharmacist site 110 may even change physical locations over time, according to some embodiments. For example, in one embodiment, a pharmacist working at a remote pharmacist site 110 in Texas may service institutional pharmacies 120 in Utah. Such a pharmacist may leave Texas and travel to another location, perhaps Colorado, and may continue to service the institutional pharmacies in Utah. For instance, the pharmacist may leave Texas after a shift of work there, and may arrive in Colorado before her next scheduled shift with the institutional pharmacies in Utah. Given the portable nature of modern computer equipment, a pharmacist may take a remote pharmacist workstation, such as illustrated in FIG. 3, while traveling between remote pharmacist sites 110, according to one embodiment.

According to some embodiments, a single remote pharmacist site 110 may service more than one institutional pharmacy 120 and a single institutional pharmacy 120 may be served by more than one remote pharmacist site 110. Additionally, more than one pharmacist may work at a remote pharmacist site 110. In general, any pharmacist at any remote pharmacist site 110 may remotely supervise and verify pharmacy work performed at any institutional pharmacy 120, according to some embodiments. For example, institutional pharmacy site 120 may be serviced by one pharmacist at remote pharmacist site 110a on Mondays and may be serviced by a different pharmacist, either at the same remote pharmacist site or a different remote pharmacist site, on Tuesdays. On Wednesdays, institutional pharmacy site 120 may be serviced by a pharmacist at remote pharmacist site 110b. Additionally, according to one embodiment, institutional pharmacy site 120 may be serviced by two (or more) different remote pharmacist sites at the same time while a single pharmacist at a remote pharmacist site may service two different institutional pharmacies at the same time.

Figure 4:
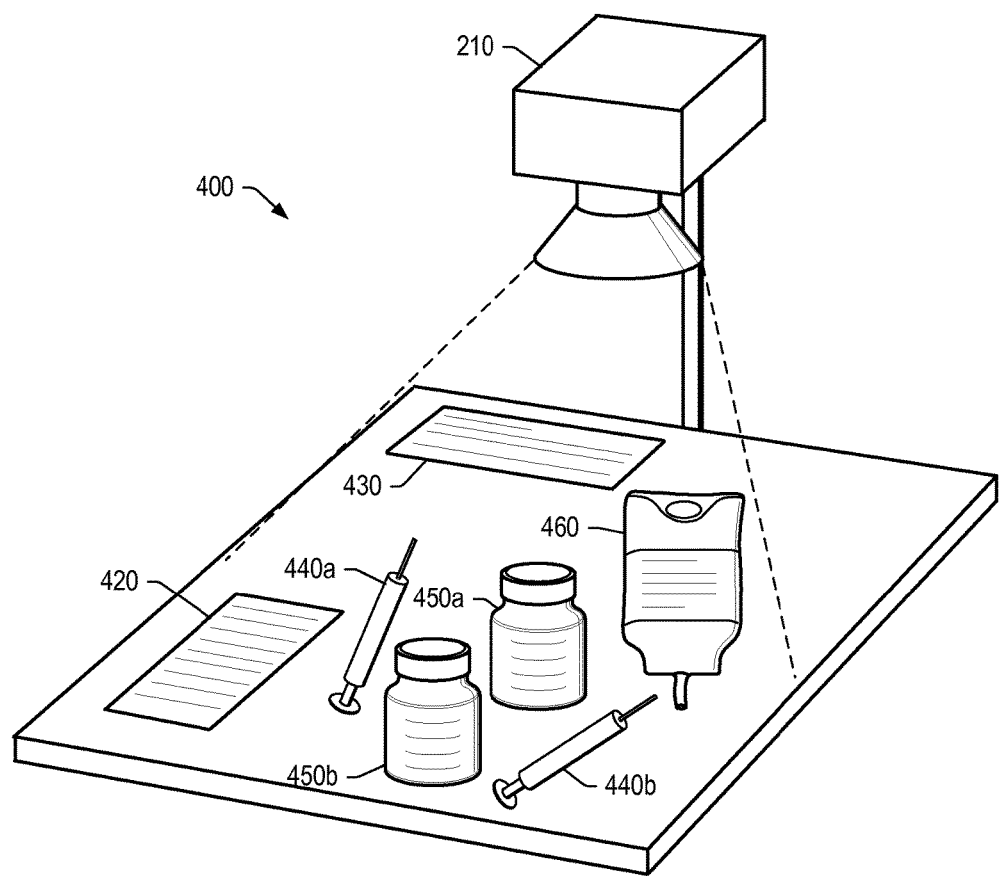
FIG. 4 illustrates an exemplary image capture device suitable for implementing remote supervision and verification of pharmacy functions, in one embodiment.

Turning now to FIG. 4, which illustrates image capture device 210 capturing an image of pharmacy work for remote supervision and verification, according to one embodiment. When a non-pharmacist worker produces pharmacy work, such as pursuant to a medication order or other pharmacy work task, one or more images of the pharmacy functions performed may be captured by image capture device 210. For instance, after performing a pharmacy function requiring supervision and verification by a pharmacist, the non-pharmacist worker may move the job to image capture device 210 and may display all materials and documentation required to properly supervise and verify correct and accurate preparation, labeling, compounding, prepackaging and/or packaging performed during the pharmacy functions, according to one embodiment. For example, in one embodiment, a non-pharmacy worker may perform one or more pharmacy functions and may capture images of the materials used, such as medicine vials 450*a* and 450*b*, syringes 440*a* and 440*b*, intravenous product 460, and documentation 420 and 430, as illustrated in FIG. 4. In some embodiments, several images may be captured as the work is performed, each capturing a different stage of the pharmacy work being performed. Additionally, one or more image may be captured of the completed work. In some embodiments, the worker may move and display the materials and documentation for image capture, while in other embodiments, images may be captured of the materials and documentation in place as they are used during the performance of pharmacy functions.

According to some embodiments, multiple captured images for a single pharmacy work task may be included in a single upload or post to a website or bulletin board, such as to system website 130. Including multiple images in single upload or post may, in certain embodiments, indicate that the images are all related to the same pharmacy work task. Alternatively, in another embodiment, each image may include a reference indicator that links the materials and documentation displayed to a corresponding pharmacy work task, such as a medication order. Such a reference indicator may be an original order, a copy of an original order, or a listing containing a unique medication order number generated from the patient's medication profile, such as a complete label, medication fill list, or a Medication Administration Record, according to various embodiments. The exact nature of such a reference indicator may vary from embodiment to embodiment or within a single embodiment. Additionally, any documentation required by policy or law for the pharmacy work performed may also be included in captured images used for remote supervision and verification. Such documentation may include, but is not limited to, the patient's name, the pharmacy location, the date and time, and/or the full signature and/or title of person performing the pharmacy functions or removing the medication from the pharmacy, according to different embodiments.

In some embodiments, a pharmacist may remotely verify pharmacy work via a real-time collaboration tool. For instance, software may be installed at both an institutional pharmacy site and at a remote pharmacist site allowing a pharmacist to view in real-time, or near real-time, images of the pharmacy work being performed. In one embodiment, a real-time collaboration tool may include software that interfaces with imaging device 210 to allow a non-pharmacist perform pharmacy work at an institutional pharmacy to transmit live images of the pharmacy work being performed. For example, the institutional pharmacy site and the remote pharmacist site may be connected over the Internet via a custom protocol for viewing remote pharmacy work, such as may be implemented by remote verification software 140 illustrated in FIG. 1. Alternatively, in another embodiment, a live feed from a camera capturing pharmacy work being performed may be transmitted to a remote pharmacist using standard, off-the-shelf, video conferencing and/or collaboration software. Thus, in some embodiments, a remote pharmacist may supervise pharmacy work as it is being performed. For example, in one embodiment, a remote pharmacist may verify each step as it is performed and may provide an indication to a non-pharmacist performing the pharmacy that the step was performed correctly. In such an example, the remote pharmacist may provide verification feedback via the same collaboration software, or via another method, such as by telephone.

Figure 5:
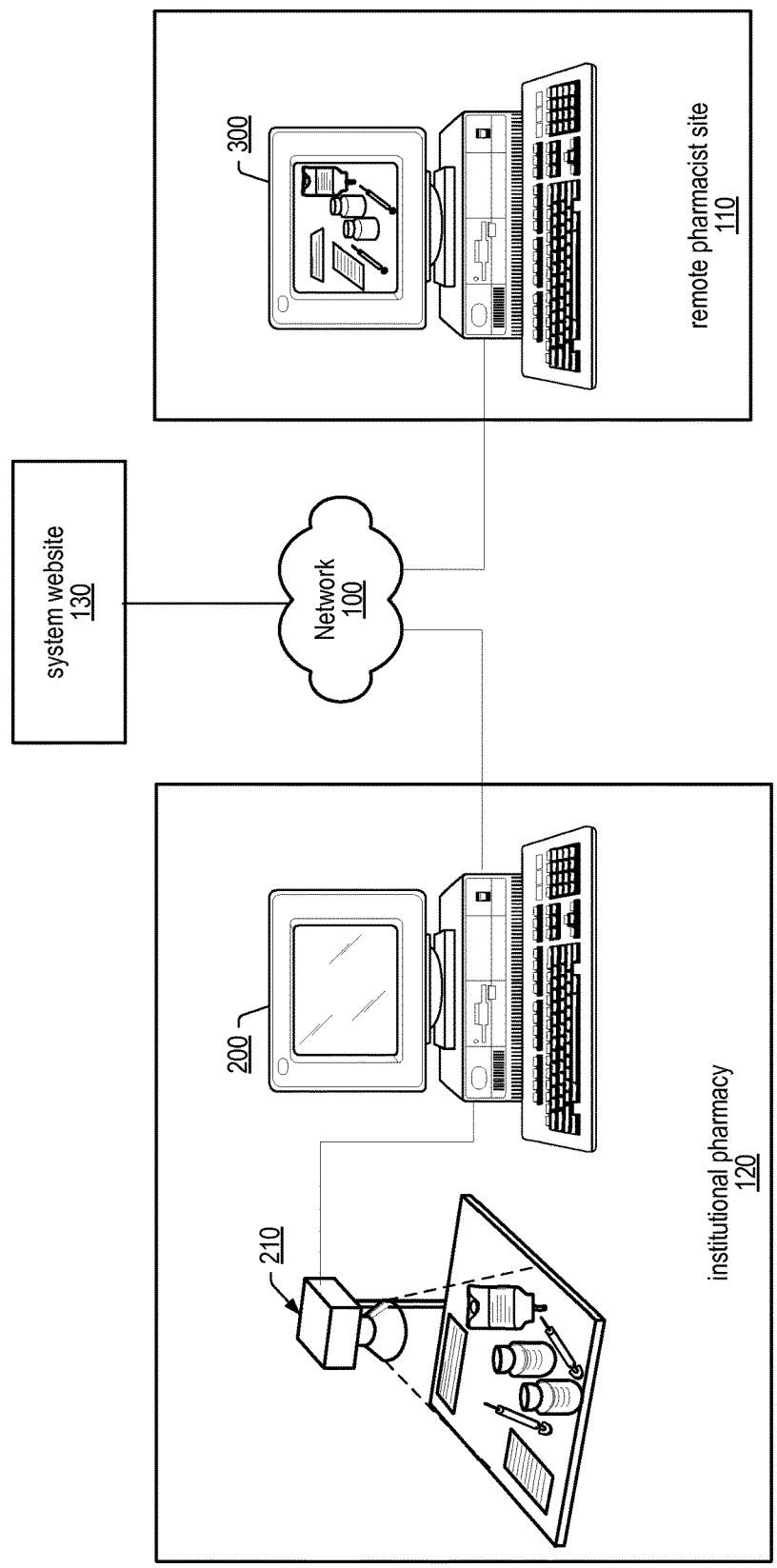
FIG. 5 illustrates an exemplary system for remotely supervising and verifying pharmacy functions, according to one embodiment.

FIG. 5 illustrates an image captured on image capture device 210 at institutional pharmacy 120 being sent and viewed at remote pharmacist site 110, in one embodiment. For example, a nurse, or other non-pharmacy personnel, at institutional pharmacy Site 120 may enter the pharmacy and compound a sterile intravenous product that was ordered for a patient after pharmacy hours and was not available outside of the pharmacy department. A pharmacist may have entered the mediation order into the patient's medication profile and may also have generated a label for the intravenous product via the pharmacy's order entry software. According to one embodiment, after visually inspecting the final product, such as for particulate matter, the nurse may place the labeled sterile intravenous product, with label and base solution content clearly visible, on image capture device 210's display area. Additionally, in one embodiment, one or more of the following items may also be placed on a display area of image capture device 210:

1. A vial of sterile water, with label clearly visible, which was used to reconstitute the medication vial added to the final product.
2. A syringe with the plunger pulled back to the marking on the syringe that indicates the volume of sterile water used to reconstitute the medication vial.
3. The vial of medication that was reconstituted, with label clearly visible, a portion of which was added to the final product's base solution.
4. A syringe with the plunger pulled back to the marking on the syringe that indicates the volume of reconstituted medication that was added to the base solution to prepare the final product.

If all the items listed above do not reasonably fit on the display area, the nurse may, in some embodiments, capture additional images that contain any items necessary to check the work performed. Additional items not listed above may also be included in captured images, such as a document with the current date and/or time, her full signature, and title, according to one embodiment.

The captured image(s) may be transmitted to system website 130 via a network or telecommunication link, according to one embodiment. Image capture device 210 may be coupled to computer 200 which itself may be coupled to network 100. In one embodiment network 100 may represent a local area network providing a connection to the Internet, while in other embodiments, network 100 may represent the Internet to which computer 200 may connect directly. The non-pharmacist worker may log onto system website 130 to upload the captured image(s), in one embodiment. The captured image(s) may be transmitted from the workstation at institutional pharmacy 120 to system website 130 and may be downloaded by a workstation at remote pharmacist site 110, according to some embodiments. In other embodiments, however, captured images may be directly transmitted to remote pharmacist site 110, via email for example. A pharmacist at remote pharmacist site 110 may view the pharmacy work performed at institutional pharmacy 120, as well as any other information necessary to conduct process checks and verify that the medication in the captured image(s) was correctly and accurately prepared, labeled, compounded, and/or packaged. Examples of information that may be included in captured images to allow supervision and verification of pharmacy work and medication removal may include, but are not limited to the following:

1. Medication labels, solution labels, final product labels.
2. Supplies used in compounding the product.
3. Equipment indicating volumes used in product preparation.
4. Indications of the order in which medications were added during product preparation.
5. Prescriber's order including patient name, drug name, dose, route of administration, schedule of drug administration, reason for administration, and signature of the prescriber or his agent.
6. Documentation that includes drug name, strength, lot number, expiration date, date, time, number of units to be removed from the pharmacy, worker initials, worker signature and title.
7. Auxiliary labels.
8. Special storage requirements for medication.
9. Drug information references.

Please note that the above list is only exemplary and that the actual items and/or the number of items included in captured images may vary from embodiment to embodiment. The pharmacist may review the captured image(s) on computer 300 to verify that the nurse recorded proper documentation for record keeping purposes, according to one embodiment.

When remotely supervising and/or verifying pharmacy work performed at institutional pharmacy 120, a pharmacist at remote pharmacist site 110 may download one or more captured images from system website 130. Alternatively, captured images may be directly transmitted from institutional pharmacy 120 to remote pharmacist site 110, as described above. The pharmacist may review the medication order entry shown on the image of the patient's Medication Administration Record in one of the captured images. He may also compare it to an image showing the actual pharmacy work performed, and may verify that an order number on the Medication Administration Record matches an order number listed on the sterile intravenous product label also shown in the captured image. The pharmacist may further inspect the captured image(s) to observe one or more of the following:

1. The label on the intravenous product is complete and correct according to the medication order, properly lists the base solution used, and has been initialed by the nurse.
2. The nurse added the correct diluent and the correct and accurate volume to reconstitute the medication vial.
3. The correct medication vial was selected for reconstitution, and that the correct and accurate volume of the reconstituted medication solution was added to the final product.
4. The intravenous product has a sterile seal on the port designed for addition of medication.
5. There is no obvious particulate matter in the solution, as seen in the image.

Please note that the above list is exemplary and that the actual steps taken by a pharmacist when remotely supervising and/or verify pharmacy functions may vary from embodiment to embodiment.

The pharmacist may also indicate that the work has been supervised and/or verified according to the captured images, and is authorized for removal from the pharmacy or to be placed into regular pharmacy stock, according to one embodiment. A pharmacist may indicate that pharmacy work has been verified in any of a number of different ways, according to various embodiments. For example, in one embodiment, a pharmacist may graphically insert a notation into one or more of the images as an indication that the work displayed in the images has been supervised and/or verified. Alternatively, a pharmacist may electronically initial one or more of the captured images. In another embodiment, the verifying pharmacist may create a document referencing the captured images and a relevant pharmacy or medication order and indication that the corresponding pharmacy work was been verified according to the captured images. Such a document may be transmitted to the institutional pharmacy or may be uploaded to and stored on system website 130, according to various embodiments.

Additionally, an electronic record or a hard copy of the verified captured image(s) may be stored at the remote pharmacist site, and/or at system website 130. In yet another example, a pharmacist may utilize digital signature technology to digitally sign one or more of the captured images or another document indicating pharmacist verification of the pharmacy work performed according to the captured images. In another embodiment, an indication that the pharmacist verified the pharmacy work according to the captured images may be transmitted to institutional pharmacy 120, either directly or indirectly. For example, a document including such an indication may be emailed or faxed to institutional pharmacy 120.

The pharmacist at a remote pharmacist site may also transmit the electronically notated image(s), or a copy thereof, from remote pharmacist site 110 to institutional pharmacy site 120 via an Internet connection, virtual private network, or any wired or wireless link, in one embodiment. This may be done to communicate to non-pharmacist personnel that the work passed supervision, is verified, and is authorized for removal from the pharmacy or to be placed into regular pharmacy stock, according to some embodiments. The image may be further notated at the institutional pharmacy 120 and an electronic or hard copy record of the supervised and verified image may be stored at institutional pharmacy 120.

Additionally, at remote pharmacist site 110, the supervised, verified, and pharmacist-initialed captured images, or other document(s) indicating that the pharmacy work was correctly verified, may be printed, such as on printer 330 and/or transmitted to institutional pharmacy 120 via facsimile or other method, such as email. The facsimile may be received in the pharmacy at institutional pharmacy 120. A nurse or other personnel may review the verified documents and verify that it has the pharmacist's initials, which may authorize her to remove the medication from the pharmacy, according to some embodiments. She may write a removal time on the papers and store them in an appropriate place so the next pharmacist on duty at the facility may review and/or file the papers for the pharmacy's records.

If, during the supervision and verification process, a pharmacist at remote pharmacist site 110 discovers, through inspection of the captured images, errors in the work performed by the non-pharmacist, the pharmacist may notify both the non-pharmacist who performed the work, as well as other supervisory personnel, about the errors so that corrective measures may be taken, according to some embodiments.

Figure 6:
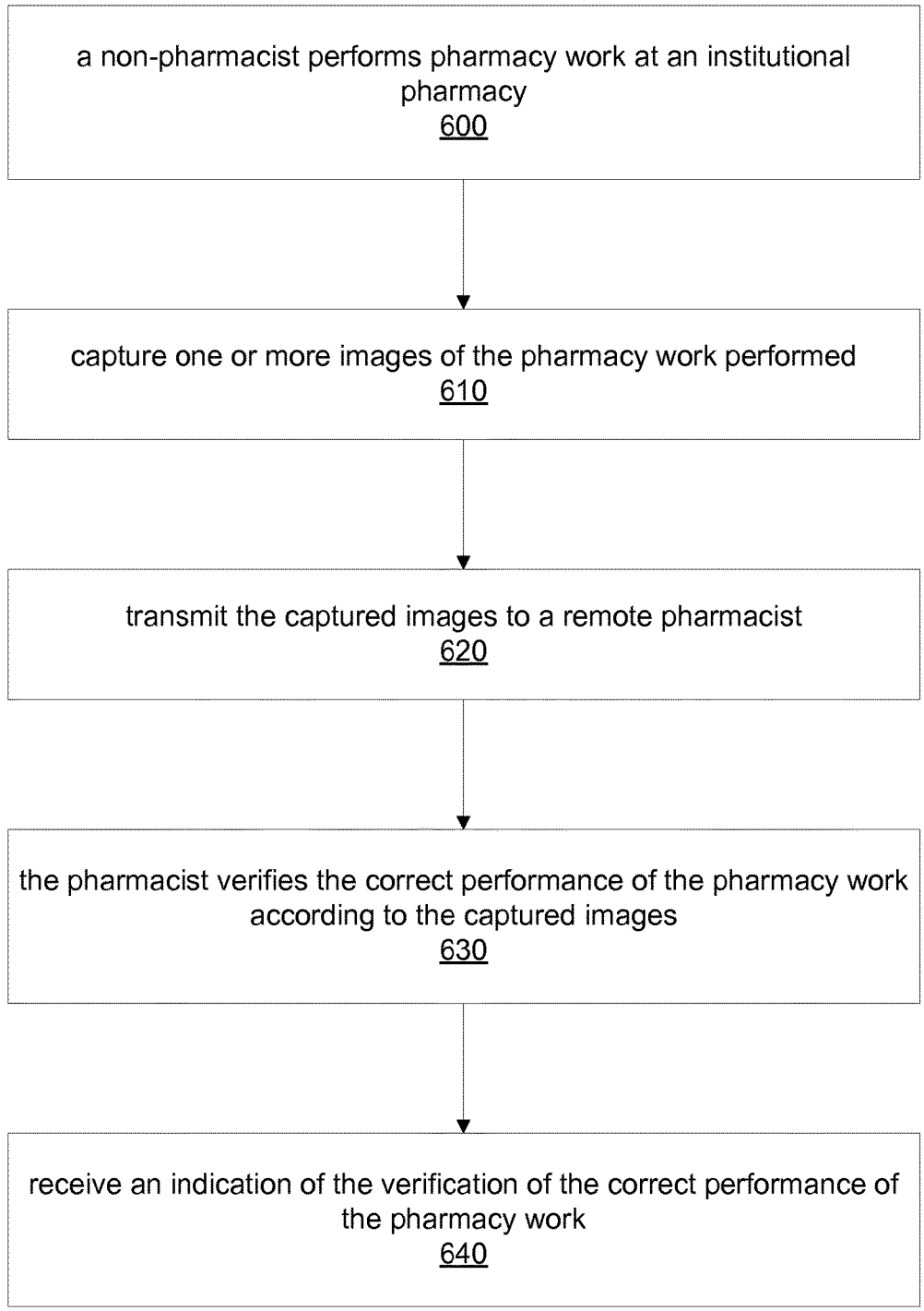
FIG. 6 is a flowchart illustrating a method for remotely supervising and verifying pharmacy functions, according to one embodiment.

FIG. 6 illustrates one embodiment of a method for remotely supervising and verifying pharmacy work performed by a non-pharmacist. As described above, a non-pharmacist may perform pharmacy work at an institutional pharmacy for a pharmacy work task requiring pharmacist supervision, verification or both, as illustrated by block 600. For instance, an institution, such as a hospital or correctional facility, may not have a pharmacist on duty all the time and a patient may require medication that can only be obtained through the institution's pharmacy. Thus, a non-pharmacist, such as a nurse or pharmacy technician, may perform the pharmacy functions required to fulfill the order. Pharmacy functions that may be remotely supervised and verified include, but are not limited to, medication preparation, packaging, prepackaging, compounding, and/or labeling of either single unit packages, multiple dose packages, in batches or in bulk. The non-pharmacist may capture one or more images of the pharmacy work, as illustrated by block 610. Images of pharmacy work may be captured at various times during the performance of the pharmacy work, in some embodiments. In other embodiments, images may be captured of the finished medication product and all materials and documentation required for the performing the pharmacy work, as described herein above.

The captured images may be transmitted to a remote pharmacist, as illustrated by block 620. Thus, as described above, the captured images may be sent to a remote pharmacist for remote supervision and review, as described above. For example, the images may be sent directly to the remote pharmacist via email, in one embodiment. In other embodiments, the captured images may be uploaded to a website from which the remote pharmacist may download them. Additionally, other documentation may also be sent to the pharmacist either by email, uploading to a website, via fax, or by any suitable means. After receiving the captured images, the remote pharmacist may verify the correct performance of the pharmacy work according to the captured images, as illustrated by block 630. For instance, the pharmacist may examine the captured images and other documents to ensure that the correct ingredients, materials, and measures were used when performing the various pharmacy functions. If the pharmacist is able to conduct process checks and verify that the pharmacy work was correctly performed, she may indicate such by initialing or digitally signing one or more of the captured images, according to one embodiment. In other embodiments, the pharmacist may indicate the verification that the pharmacy work was correctly performed according to the captured images by creating a separate verification document or record. The pharmacist may send such verification to the institutional pharmacy.

The institutional pharmacy may receive an indication of the verification of the correct performance of the pharmacy work, as illustrated by block 640. For instance, the pharmacist may email an indication that the pharmacy work was verified, or alternatively, may upload such an indication to system website 130 from which the institutional pharmacy may download it, according to different embodiments. Alternatively, in another embodiment, the pharmacist may fax such an indication to the institutional pharmacy. After receiving an indication that the remote pharmacist verified the pharmacy work, the medication or other pharmacy product produced by the pharmacy work may be further processed or removed from the pharmacy.

Figure 7:
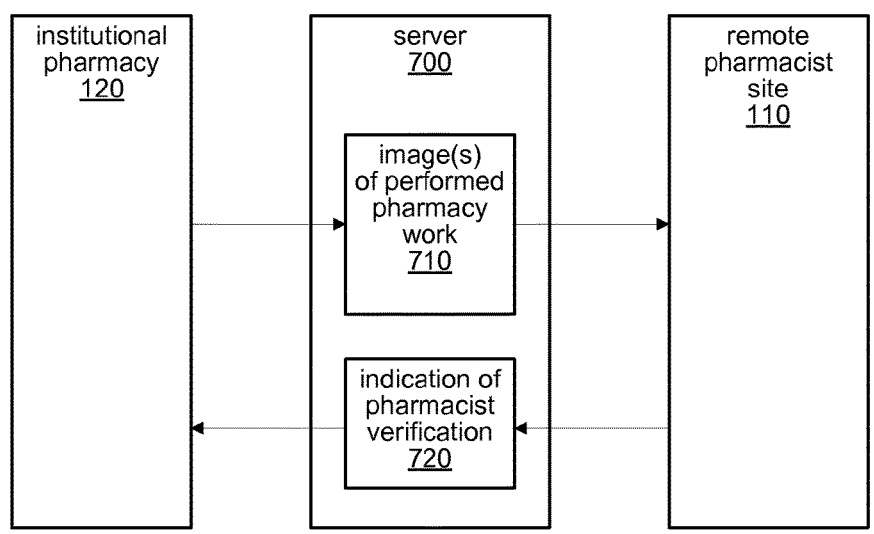
FIG. 7 is a block diagram illustrating a server facilitating remote supervision and verification of pharmacy functions, in one embodiment.

As noted above, in some embodiments, a remote pharmacist may remotely supervise and verify pharmacy functions according to images of the performed pharmacy work that transmitted directly between an institutional pharmacy and the remote pharmacist. In other embodiments, however, institutional pharmacies and remote pharmacists may use a network addressable server, such as may be part of system website 130, to communicate and transfer images and/or other data or documents related to remotely verifying pharmacy functions. FIG. 7 is a block diagram illustrating the use of server 700 by institutional pharmacy 120 and remote pharmacist site 110 for communication and data (image) exchange as part of remote verification of pharmacy functions. Server 700 may be located at institutional pharmacy 120, remote pharmacist site 110, or at a location separate from either institutional pharmacy 120 or remote pharmacist site 110, according to various embodiments. Server 700 may be addressable via network 100, which in some embodiments, may be the Internet. In other embodiments, however, server 700 may be accessible via other methods, such as via a corporate LAN/WAN, direct modem communication, or other wired or wireless technology. In some embodiments, server 700 may be a web server, while, in other embodiments, server 700 may be a bulletin board system allowing posts and retrieval of images and/or other documents. Server 700 may provide security, such as requiring user names and passwords, or other user authentication, to prevent unauthorized accessing of pharmacy related images or information. In general, server 700 may utilize any of numerous data and communication security techniques, such as encryption, user authentication, HTTPS communication, etc.

When utilizing a server, such as server 700, for communication related to remote verification of pharmacy functions, the non-pharmacist performing the pharmacy work may upload or transmit one or more images of performed pharmacy work (or, alternatively, images of the work as it is being performed), to server 700. For example, in one embodiment, images may be transmitted via FTP or another network file transfer protocol. Server 700 may then store the received images for later access by a remote pharmacist. In some embodiments, the images may be associated with a job or task identifier that may be used by a pharmacist to reference the images for review.

Server 700 may also provide an interface for review of images by pharmacists, according to some embodiments. For instance, server 700 may notify the pharmacist that the images have been stored and are available for review. Server 700 may also allow the pharmacist to download or otherwise retrieve the images from server 700 for review locally on the pharmacist's computer. Alternatively, in another embodiment, server 700 may provide an interface for online reviewing of images. For example, server 700 may generate web pages allowing a pharmacist to view the stored images of performed pharmacy work with a standard web browser program without having to retrieve or save the images locally.

After reviewing the images to verify whether the pharmacy work was performed correctly, a pharmacist may upload to server 700 an indication of the verification, according to the images, of the pharmacy work performed. For example, in one embodiment, the pharmacist may upload a copy of one or more of the images to which the pharmacist's digital signature is attached as an indication of the verification of the pharmacy work. In another embodiment, however, the pharmacist may upload a separate document including an indication of his verification of the pharmacy work. In yet another embodiment, server 700 may provide an interface, such as via generated web pages, allowing a pharmacist to record on server 700 an indication of the verification of the pharmacy work according to the images.

Server 700 also may, in some embodiments, notify the non-pharmacist that the pharmacist has recorded or uploaded an indication of the verification of the pharmacy work. Thus, server 700 may direct the communication between the non-pharmacist at the institutional pharmacy and the remote pharmacist. Additionally, server 700 may provide an interface for the institutional pharmacy to access, view, and/or download the pharmacist's indication that the pharmacy work was verified. Server 700 may provide an interface allowing the non-pharmacist or institutional pharmacy to download whatever data or documents were stored on server 700 by the pharmacist, according to one embodiment. Alternatively, server 700 may allow personnel at the institutional pharmacy to view data and/or documents from the remote pharmacist site online without having to download and store them locally at the institutional pharmacy. For example, in one embodiment, server 700 may generate web pages allowing review of data and/or documents stored on server 700 by a remote pharmacist.

Using a server, or other shared storage area, for communication between an institutional pharmacy and a remote pharmacist may also facilitate review and/or supervision of the remote verification process by administrators or others. For instance, server 700 may provide an interface allowing a director of an institutional pharmacy to access, examine and/or review the images from the institutional pharmacy as well as any data or documents from remote pharmacists. Additionally, server 700 may be configured to work in conjunction with other software on workstations at institutional pharmacies and/or remote pharmacist sites. For example, custom software, such as remote verification software 140, configured specifically for communication and data exchange as part of remote verification of pharmacy functions may provide a user interface for uploading, downloading, and/or reviewing images stored on server 700, according to one embodiment.

Figure 8:
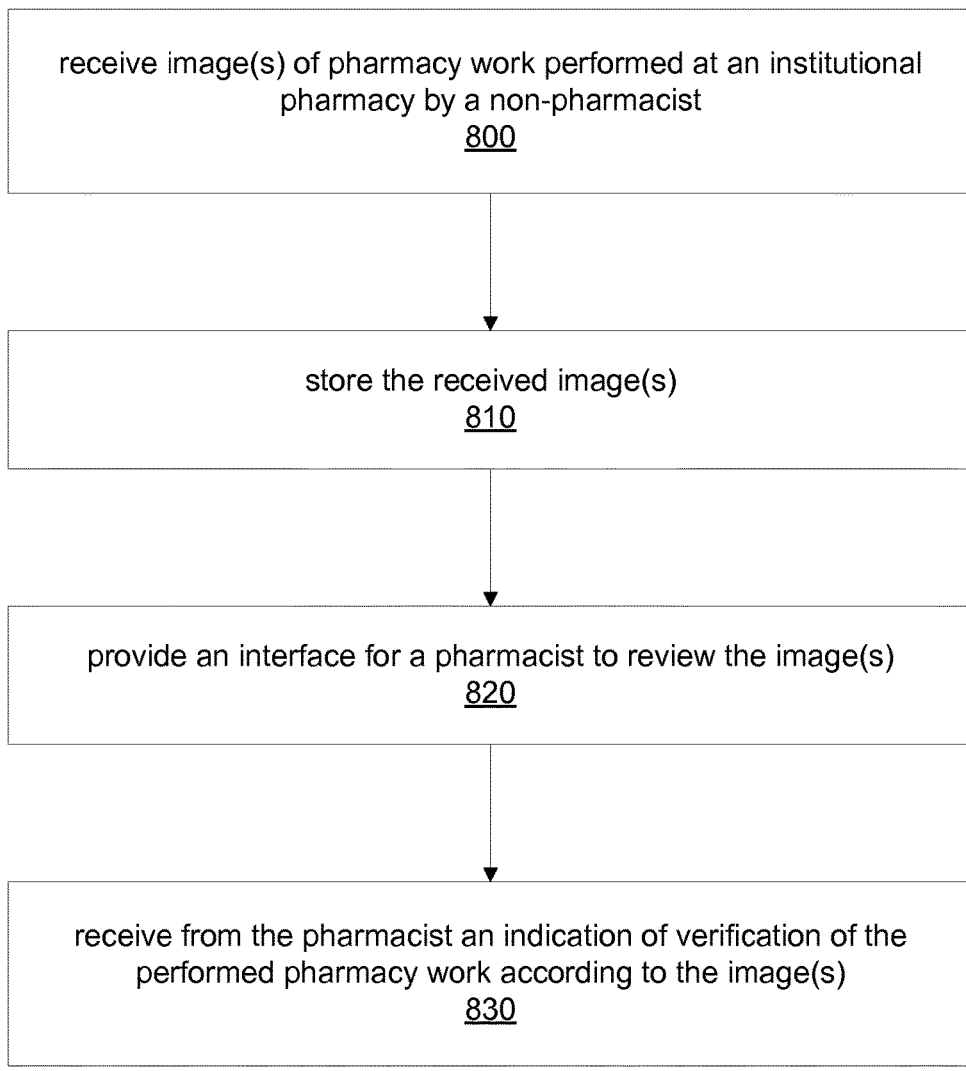
FIG. 8 is flowchart illustrating one embodiment of a method for utilizing a network accessible server for remote supervision and verification of pharmacy functions.

FIG. 8 illustrates a flowchart for one embodiment of a method for a server, such as server 700 described above, to facilitate remote supervision of pharmacy functions, as described herein. For instance, server 700 may receive one or more images of pharmacy work performed by a non-pharmacist at an institutional pharmacy, such as institutional pharmacy 120, as illustrated by block 800. As noted above, images of performed pharmacy work maybe uploaded, posted, or otherwise transmitted to server 700. Server 700 may store the received images for later access, retrieval, and/or review, as illustrated by block 810. Server 700 may store received images in any of variety of manners and formats, according to various embodiments. Images may be stored as individual files on a file server, as records in an image database, or multiple images may be compacted and stored together in a single file, such as in a .ZIP file, in some embodiments.

Server 700 may also provide an interface for a remote pharmacist, such as one at remote pharmacist site 110, to review the images, as illustrated by block 820. For example, in one embodiment, server 700 may provide a web interface, consisting of one or more generated web pages, allowing a remote pharmacist to review images using a standard web browser program. In another embodiment, server 700 may implement a messaging interface allowing custom software for remote verification of pharmacy functions, such as remote verification software 140, to send messages requesting the storage or retrieval of images, documents or other data. In general, server 700 may allow a remote pharmacist to access the images stored on server 700 by an institutional pharmacy.

After reviewing the pharmacy work according to the images, a pharmacist may record or store on server 700 an indication of his verification of the pharmacy work. Thus, server 700 may receive from the pharmacist an indication of verification of the performed pharmacy work according to the images, as illustrated by block 830. In some embodiments, server 700 may provide an interface allowing the pharmacist to record such an indication. In another embodiments, the pharmacist may upload a document or image including such an indication. For example, the pharmacist may attach a digital signature or other digital certificate to one or more of the images and upload the image(s) to server 700 and the institutional pharmacy may be able to download or otherwise access the pharmacist's indication. Alternatively, the pharmacist may generate and store a separate document including an indication of the verification of the performed pharmacy work. In some embodiments, such a document may include details of the verification or may include issues or problems discovered in the performance of the pharmacy functions.

Server 700 may, in some embodiments, notify an institutional pharmacy, such as via email or instant messenger, that the pharmacist has finished reviewing the stored images and has recorded an indication of his verification of the pharmacy function according to the images. Additionally, server 700 may implement or provide an interface allowing an institutional pharmacy to access and/or review results of the pharmacist's verification. For example, in one embodiment, server 700 may allow custom software, such as remote verification software 140 to access and/or download the data or documents stored by a remote pharmacist. Alternatively, server 700 may implement a web page based interface allowing an institutional pharmacy to review data and/or documents stored on server 700 by a remote pharmacist.

Figure 9:
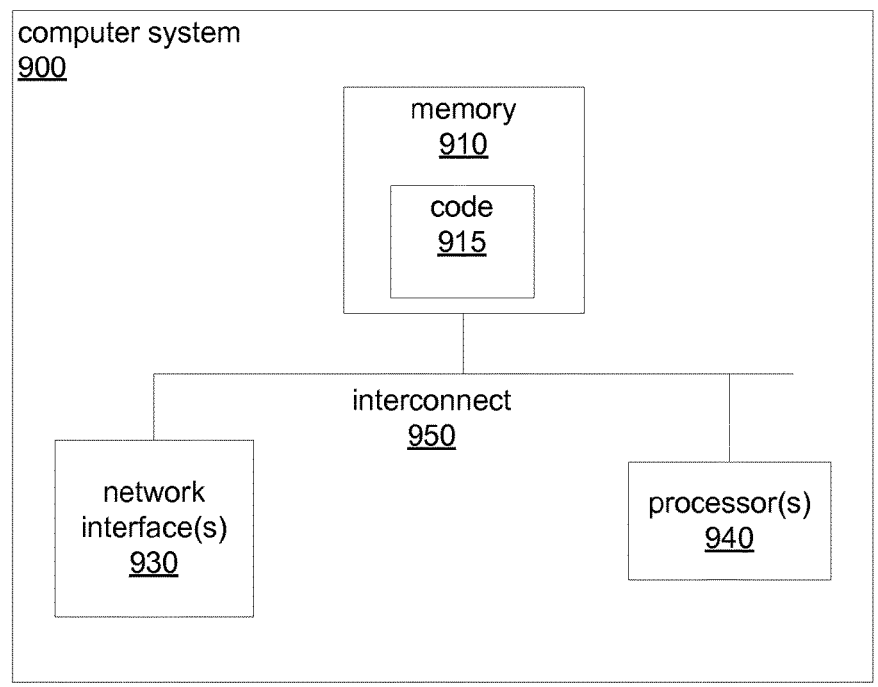
FIG. 9 is a block diagram illustrating an exemplary computer system suitable for implementing remote supervision and verification of pharmacy functions, according to one embodiment.

FIG. 9 is a block diagram illustrating an embodiment of a computer system usable to implement remote pharmacy supervision and verification. In some embodiments, a workstation at either institutional pharmacy 120, remote pharmacist site 110, system website 130, and/or server 700, may include a general-purpose computer system that includes or is configured to access one or more computer-accessible media, such as computer system 900 illustrated in FIG. 9. In the illustrated embodiment, computer system 900 includes one or more processors 940 coupled to a system memory 910 via an interconnect 950. Computer system 900 may further includes a network interface 930 also coupled to interconnect 950.

In various embodiments, computer system 900 may be a uniprocessor system including one processor 940, or a multiprocessor system including several processors 940 (e.g., two, four, eight, or another suitable number). Processors 940 may be any suitable processors capable of executing instructions. For example, in various embodiments, processors 940 may be general-purpose or embedded processors implementing any of a variety of instruction set architectures (ISAs), such as the x86, PowerPC, SPARC, or MIPS ISAs, or any other suitable ISA. In multiprocessor systems, each of processors 940 may commonly, but not necessarily, implement the same ISA.

System memory 910 may be configured to store instructions and data accessible by processor 940. In various embodiments, system memory 910 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those methods and techniques described above for remotely supervising and verifying pharmacy functions, may be stored within system memory 910 as code 915.

In one embodiment, interconnect 950 may be configured to coordinate I/O traffic between processor 940, system memory 910, and any peripheral devices in the device, including network interface 930 or other peripheral interfaces. In some embodiments, interconnect 950 may perform any necessary protocol, timing or other data transformations to convert data signals from one component (e.g., system memory 910) into a format suitable for use by another component (e.g., processor 940). In some embodiments, interconnect 950 may include support for devices attached through various types of peripheral buses, such as a variant of the Peripheral Component Interconnect (PCI) bus standard or the Universal Serial Bus (USB) standard, for example. In some embodiments, the function of interconnect 950 may be split into two or more separate components, such as a north bridge and a south bridge, for example. Also, in some embodiments some or all of the functionality of interconnect 950, such as an interface to system memory 910, may be incorporated directly into processor 940.

Network interface 930 may be configured to allow data to be exchanged between computer system 900 and other devices attached to a network, such as other computer systems, for example. Network interface 930 may commonly support one or more wireless networking protocols (e.g., Wi-Fi/IEEE 802.11, or another wireless networking standard). However, in various embodiments, network interface 930 may support communication via any suitable wired or wireless general data networks, such as other types of Ethernet network, for example. Additionally, network interface 930 may support communication via telecommunications/telephony networks such as analog voice networks or digital fiber communications networks, via storage area networks such as Fibre Channel SANs, or via any other suitable type of network and/or protocol.

In some embodiments, system memory 910 may be one embodiment of a computer-accessible medium configured to store program instructions and data as described above. However, in other embodiments, program instructions and/or data may be received, sent or stored upon different types of computer-accessible media. Generally speaking, a computer-accessible medium may include storage media or memory media such as magnetic or optical media, e.g., disk or DVD/CD coupled to computer system 1100 via interconnect 950. A computer-accessible medium may also include any volatile or non-volatile media such as RAM (e.g. SDRAM, DDR SDRAM, RDRAM, SRAM, etc.), ROM, etc, that may be included in some embodiments of computer system 900 as system memory 910 or another type of memory. Further, program instructions or data on a computer-accessible medium may be transmitted via transmission media or signals such as electrical, electromagnetic, or digital signals, conveyed via a communication medium such as a network and/or a wireless link, such as may be implemented via network interface 930.

The various methods as illustrated in the figures and described herein represent exemplary embodiments of methods. The methods may be implemented manually, in software, in hardware, or a combination thereof. The order of any method may be changed, and various elements may be added, reordered, combined, omitted, modified, etc. Additionally, various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system for remotely verifying the correct preparation of a sterile compounded medication in a sterile pharmacy work area at an institutional pharmacy, comprising:
    (a) an image capture device arranged to capture a plurality of images of at least one portion of the sterile pharmacy work area during sterile compounding of a medication performed by a non-pharmacist person, including one or more material components and labels provided thereon;
    (b) a first computer in communication with a pharmacy order entry system, a server, the image capture device, and an input device, the first computer comprising at least one processor and a display device, the first computer programmed or configured to:
        i. display at least one medication order received from the pharmacy order entry system on said display device;
        ii. capture a first image with the image capture device during a first step of preparation of the sterile compounded medication;
        iii. associate the first image with information relating to the at least one medication order;
        iv. transmit the first image to the server;
        v. receive a verification from the server that the first step was performed correctly;
        vi. after receiving the verification from the server, capture a second image with the image capture device during a second stage of preparation of the sterile compounded medication;
        vi. associate the second image with information relating to the at least one medication order;
        vii. transmit the at least one image and information relating to the at least one medication order to the server;
        viii. receive a verification from the server that the second step was performed correctly; and
        ix. receive authorization to place the sterile compounded medication into pharmacy stock; and
    (c) verification software executable on the server programmed or configured to (i) transmit to a remote pharmacist computer a notification that the first image is ready for review, (ii) generate a user interface on the remote pharmacist computer configured to display the first image for review and receive a first indication that preparation of the first stage of preparation of the sterile compounded medication was performed correctly or incorrectly, (iii) receive and record the indication, (iv) transmit the first indication to at least one of the first computer and a second computer, (v) transmit to the remote pharmacist computer a notification that the second image is ready for review, (vi) generate a user interface on the remote pharmacist computer configured to display the second image for review and receive a second indication that preparation of the second stage of preparation of the sterile compounded medication was performed correctly or incorrectly, (vii) transmit the second indication to at least one of the first computer and a second computer, (viii) receive authorization to place the sterile compounded medication into pharmacy stock, and (ix) transmit the authorization to the first computer.

2. The system of claim 1, wherein the first computer transmits the at least one image of the preparation of the sterile compounded medication to the server as a single batch after the sterile compounded medication has been prepared.

3. The system of claim 1, wherein the institutional pharmacy is a hospital pharmacy.

4. The system of claim 1, wherein the verification software is programmed or configured to send a notification to the remote pharmacist computer that the at least one image of preparation of the sterile compounded medication is ready for review, and the remote pharmacist computer displays the notification.

5. The system of claim 1, wherein the at least one image is stored on the server.

6. The system of claim 1, wherein, when the indication comprises an indication that preparation of the sterile compounded medication has been performed incorrectly, the indication further comprises details as to one or more errors with the preparation.

7. The system of claim 1, wherein the verification software on the server is programmed or configured to send a notification to the first computer or the second computer that the indication has been received from the remote pharmacist computer, and wherein the first computer or the second computer displays the notification.

8. The system of claim 1, wherein the at least one image comprises at least one image of a vial of reconstituting media and a syringe containing a specific volume of the reconstituting media and wherein the at least one image comprises a second image comprising a second syringe containing a specific volume of the reconstituting media.

9. The system of claim 1, wherein the at least one image comprises a vial of prepackaged stock medication.

10. The system of claim 1, wherein the first computer comprises a non-transitory computer-readable medium comprising program instructions that, when executed by the at least one processor, cause the at least one processor to:
encrypt the at least one image of preparation of the sterile compounded medication and information associated with the at least one medication order to produce encrypted data; and
transmit the encrypted data from the first computer to the server for storage thereon.

11. The system of claim 1, wherein the at least one medication order is a patient-specific medication order.

12. The system of claim 1, wherein the at least one medication order is not related to a specific order.

13. The system of claim 12, wherein the at least one medication order is for a batch preparation.

14. The system of claim 1, wherein the at least one image comprises one or more of: medication labels, solution labels, final product labels, supplies used in compounding the sterile medication, equipment indicating volumes used in compounding the sterile medication, indications of the order in which medications or solutions were added during compounding of the sterile medication, and prescription information.

15. A computer-implemented method for remotely verifying the correct preparation of a sterile compounded medication in a sterile pharmacy work area at an institutional pharmacy, comprising:
receiving at least one medication order from a pharmacy order entry system;
generating at least one graphical user interface comprising the at least one medication order;
capturing, with at least one image capture device during a first stage of preparation of a sterile compounded medication, a first image of at least one portion of the sterile pharmacy work area, wherein the first image comprises:
a syringe having a withdrawn plunger indicating a particular volume of a material component of the sterile compounded medication,
a label of the material component;
capturing, with the at least one image capture device during a second stage of preparation of the sterile compounded medication, a second image of at least one portion of the sterile pharmacy work area, wherein the second image comprises:
a container comprising the sterile compounded medication; and
a label of the sterile compounded medication;
associating information relating to the at least one medication order with the first image and the second image;
transmitting, from the first computer at the institutional pharmacy to the server, the second image and the information relating to the at least one medication order;
generating a notification to the remote pharmacist computer that the first image, second image, and associated information have been transmitted to the server and are ready for review;
receiving an indication, at the server and from the remote pharmacist computer, that the preparation of the sterile compounded medication was performed correctly;
generating a notification to the first computer or a second computer at the institutional pharmacy that the preparation of the sterile compounded medication was performed correctly; and
displaying, on the first computer or a second computer, the notification that the preparation of the sterile compounded medication was performed correctly.

16. A computer-implemented method for remotely verifying the correct preparation of a sterile compounded medication in a sterile pharmacy work area at an institutional pharmacy, comprising:
receiving, with a first computer at the sterile pharmacy work area, at least one medication order from a pharmacy order entry system;
generating, on a display of the first computer, at least one graphical user interface comprising the at least one medication order;
capturing, with at least one image capture device during a first stage of preparation of a sterile compounded medication, a first image, wherein the image comprises:
a container comprising a material component of the sterile compounded medication;
a label of the material component, including an expiration date for the material component;
a syringe having a withdrawn plunger indicating a particular volume of the material component of the sterile compounded medication; and
a label comprising prescription information;
encrypting and transmitting the first image from the first computer at the sterile pharmacy work area to a server;
generating, in response to entry of a username and password on a remote pharmacist computer, a user interface on a display of the remote pharmacist computer to display the first image;
notifying the remote pharmacist computer that the first image is ready for review;
receiving an indication, at the server and from the remote pharmacist computer, that the material component and the particular volume of the material component are correct;
notifying the first computer that the particular volume of the material component is correct;
displaying, on the first computer, an indication that the particular volume of the material component is correct;
capturing, with the at least one image capture device during a second stage of preparation of the sterile compounded medication, a second image of at least one portion of the sterile pharmacy work area, wherein the second image comprises:
  a container comprising the sterile compounded medication; and
  a label comprising prescription information;
encrypting and transmitting, from the first computer at the institutional pharmacy to the server, the second image and the information relating to the at least one medication order;
notifying the remote pharmacist computer that the second image is ready for review;
receiving an indication, at the server and from the remote pharmacist computer, that the second stage of preparation of the sterile compounded medication was performed correctly;
notifying the first computer or a second computer at the institutional pharmacy that the second stage of preparation of the sterile compounded medication was performed correctly; and
displaying, on the first computer or a second computer, a notification that the second stage of preparation of the sterile compounded medication was performed correctly.

17. The system of claim 1, wherein the first computer is programmed or configured to modify the first image by overlaying an identifier relating to the at least one medication order.

* * * * *

UNITED STATES PATENT AND TRADEMARK OFFICE
CERTIFICATE OF CORRECTION

PATENT NO. : 10,417,758 B1
APPLICATION NO. : 13/747231
DATED : September 17, 2019
INVENTOR(S) : Emily H. Alexander Page 1 of 1

It is certified that error appears in the above-identified patent and that said Letters Patent is hereby corrected as shown below:

On the Title Page

Column 2, Item (57) ABSTRACT, Line 9, after "types" insert -- of --

Column 2, Item (57) ABSTRACT, Line 15, after "copy" insert -- of --

In the Claims

Column 18, Line 26, Claim 1, delete "vi." and insert -- vii. --

Column 18, Line 28, Claim 1, delete "vii." and insert -- viii. --

Column 18, Line 31, Claim 1, delete "viii." and insert -- ix. --

Column 18, Line 33, Claim 1, delete "ix." and insert -- x. --

Signed and Sealed this
Third Day of December, 2019

Andrei Iancu
*Director of the United States Patent and Trademark Office*

UNITED STATES PATENT AND TRADEMARK OFFICE
CERTIFICATE OF CORRECTION

PATENT NO. : 10,417,758 B1
APPLICATION NO. : 13/747231
DATED : September 17, 2019
INVENTOR(S) : Emily H. Alexander It is certified that error appears in the above-identified patent and that said Letters Patent is hereby corrected as shown below:

In the Claims

Column 18, Line 14, Claim 1, delete "step" and insert -- stage --

Column 18, Line 20, Claim 1, delete "step" and insert -- stage --

Column 18, Line 27, Claim 1, delete "the at least one image" and insert -- the second image --

Column 18, Line 31, Claim 1, delete "step" and insert -- stage --

Column 18, Line 59, Claim 2, delete "the at least one image" and insert -- the second image --

Column 18, Line 67, Claim 4, delete "the at least one image" and insert -- at least one of the plurality of images --

Column 19, Line 4, Claim 5, delete "the at least one image" and insert -- at least one of the plurality of images --

Column 19, Line 6, Claim 6, between 'the' and 'indication' insert -- first --

Column 19, Line 6, Claim 6, after "indication" insert -- or the second indication --

Column 19, Line 8, Claim 6, after "the" insert -- first --

Column 19, Line 9, Claim 6, after "indication" insert -- or the second indication --

Column 19, Line 14, Claim 7, between 'the' and 'indication' insert -- first --

Column 19, Line 14, Claim 7, after "indication" insert -- or the second indication --

Signed and Sealed this
Twenty-third Day of May, 2023

Katherine Kelly Vidal
*Director of the United States Patent and Trademark Office*

CERTIFICATE OF CORRECTION (continued)
U.S. Pat. No. 10,417,758 B1

Column 19, Line 17, Claim 8, delete "the at least one image" and insert -- the plurality of images --

Column 19, Line 18, Claim 8, delete "at least one image" and insert -- the first image --

Column 19, Line 20, Claim 8, delete "the at least one image" and insert -- the plurality of images --

Column 19, Line 21, Claim 8, delete "a second image" and insert -- the second image --

Column 19, Line 23, Claim 9, delete "the at least one image" and insert -- at least one of the plurality of images --

Column 19, Line 29, Claim 10, delete "the at least one image" and insert -- the plurality of images --

Column 19, Line 41, Claim 14, delete "the at least one image" and insert -- at least one of the plurality of images --

Column 20, Lines 13 & 14, Claim 15, delete "the remote pharmacist computer" and insert -- a remote pharmacist computer --